United States Patent [19]

Takalo et al.

[11] Patent Number: 5,571,897
[45] Date of Patent: Nov. 5, 1996

[54] LUMINESCENT LANTHANIDE CHELATES

[75] Inventors: Harri Takalo, Turku; Veli-Matti Mukkala, Kaarina, both of Finland

[73] Assignee: Wallac Oy, Turku, Finland

[21] Appl. No.: 244,659

[22] PCT Filed: Dec. 5, 1991

[86] PCT No.: PCT/FI91/00373

§ 371 Date: Jul. 26, 1994

§ 102(e) Date: Jul. 26, 1994

[87] PCT Pub. No.: WO93/11433

PCT Pub. Date: Jun. 10, 1993

[51] Int. Cl.[6] .............................. C07F 5/00; C07J 21/00; C07D 401/50; C07D 413/00
[52] U.S. Cl. .............................. 534/15; 534/16; 540/465; 540/467; 540/470; 540/474; 540/480; 540/481; 546/2; 546/5; 546/256; 546/270.4; 546/271.4; 546/274.1; 546/275.4; 546/276.4; 546/272.4; 546/269.4; 546/283.4; 546/6; 546/332; 546/313; 546/323
[58] Field of Search .......................... 534/15, 16; 546/2, 546/5, 256, 275, 276, 277, 278, 279, 280, 281, 283, 6; 540/465, 467, 470, 474, 480, 481

[56] References Cited

U.S. PATENT DOCUMENTS

| | | | |
|---|---|---|---|
| 4,761,481 | 8/1988 | Hale et al. | 546/296 |
| 4,837,169 | 6/1989 | Toner | 436/546 |
| 4,925,804 | 5/1990 | Hale et al. | 436/501 |
| 4,927,923 | 5/1990 | Mathis et al. | 540/456 |
| 5,032,677 | 7/1991 | Hale et al. | 530/402 |
| 5,324,825 | 6/1994 | Kankare et al. | 534/16 |
| 5,346,996 | 9/1994 | Lehn et al. | 534/15 |

FOREIGN PATENT DOCUMENTS

| | | |
|---|---|---|
| 0321353A1 | 6/1989 | European Pat. Off. |
| WO90/00550 | 1/1990 | WIPO |

OTHER PUBLICATIONS

Okamoto et al., *Polyhedron* vol. 3, No. 5, 1984, pp. 635–638.
Schilt et al., *Talanta*, vol. 24, 1977, pp. 685–687.

*Primary Examiner*—John Kight
*Assistant Examiner*—Lara E. Chapman
*Attorney, Agent, or Firm*—Ronald J. Kubovcik

[57] ABSTRACT

Lanthanide chelates which contain three heterocyclic rings covalently coupled to each other (either one 2,6-pyridylene and two five-membered unsaturated heterocyclic ring moieties or two 2,6-pyridylene and one five-membered unsaturated heterocyclic ring moiety) and two chelating groups so seated that they together chelate the same lanthanide ion even in aqueous solutions. These lanthanide chelates can optionally contain a reactive group for coupling to biologically active molecules. The new chelates are suitable for classical lanthanide chelate applications and are also useful as probes in time-resolved fluorescence microscopy, cytometry, multilabelling techniques and in process controls in industry.

8 Claims, No Drawings

LUMINESCENT LANTHANIDE CHELATES

This application is a 371 of PCT/FI91/00373 filed Dec. 5, 1991, WO93/11433.

FIELD OF THE INVENTION

The invention pertains no new luminescent lanthanide chelates comprising three unsaturated heterocyclic rings covalently coupled to each other and additionally comprising two chelating groups. This structure of three heterocyclic rings is formed of one or two 2,6-pyridylene moieties and five-membered unsaturated heterocyclic rings.

The new chelates of our invention find applications in those areas that are classical for lanthanide chelates and known in the art. Moreover, these compounds are useful as probes in time-resolved fluorescence microscopy, cytometry, multilabelling techniques and process controls in industry.

DESCRIPTION OF THE PRIOR ART

In immunoassays and DNA hybridization assays time-resolved luminescence spectroscopy using lanthanide chelates is well known ( e g. I. A. Hemmilä, "Applications of Fluorescence in Immunoassays" in J. D. Winefordner and I. M. Kolthoff, Eds., *Chemical Analysis*; Vol 117, John Wiley & Sons, Inc., USA, 1991 and the references therein). Stable luminescent lanthanide chelates also have other applications, e.g. fluorescence microscopy and cytometry. Because of their paramagnetic properties, these lanthanide chelates are useful as sensitive probes in magnetic resonance imaging (MRI). The radioactive isotopes of metals such as indium and stable chelating ligands on the macromolecules offer possibilities to use the ligands of this invention in the treatment of diseases such as cancer.

Luminescent lanthanide chelates have previously been proposed [macropolycycles: French Patent No. 2,570,703 (1986) and Eur. Patent Appl. 321,353 (1988); phenols: U.S. Pat. No. 4,670,572 (1987); coumarines: U.S. Pat. No. 4,801,722 (1989) and U.S. Pat. No. 4,794,191 (1988); polypyridines: U.S. Pat. No. 4,837,169 (1989), U.S. Pat. No. 4,859,777 (1989), Int. Pat. Appl. PCT/SE89/00073 (1989) and Int. Pat. Appl. PCT/SE89/00379 (1989); aryl pyridines: U.S. Pat. 4,761,481 (1988) and Int. Pat. Appl. PCT/WO89/04826; ethynyl pyridines: U.S. Pat. No. 4,920,195 (1990); phenanthrolines: U.S. Pat. No. 4,772,563 (1988); salicylates: M. P. Bailey, B. F. Rocks and C. Riley, Analyst, 109, 1449 (1984)].

Stable luminescent lanthanide chelates, whose energy absorbing group comprises either one 2,6-pyridylene and two five-membered unsaturated heterocyclic ring moieties, or two 2,6-pyridylene moieties and one five-membered unsaturated heterocyclic ring moiety coupled to each other with a covalent bond between the carbon atoms, are non known. Some basic structures comprising three heterocyclic rings covalently coupled to each other (including one or two pyridine rings) have been synthesized (see e.g. V. Nair and K. H. Kim, *J. Heterocyclic Chem.* 13 (1976), 873; S. Kubota and H. Ohtsuka, *Tokushima Daigcaku Yakugaku Kenkyu Nempo* 9 (1963) 15, CA58:2449a; J. F. Geldhard and F. Lions, *J. Org. Chem.* 30 (1965) 318; R. Menasse, G. Klein an H. Erlenmeyer, *Helv. Chim. Acta*, 38 (1955) 1289; H. A. Goodwin, *Aust. J. Chem* 17 (1964) 1366; R. J. Clark and J. Walker, *J. Chem. Soc.C* 6 (1966) 1354; S. Gronowitz and D. Peters, *Heterocycles* 30(1) (1990) 645 and A. T. Parker, P. Singh and V. Vignevich, *Aust. J. Chem.* 44 (1991) 1041). As such, these compounds are not stable enough for use with lanthanide ions in aqueous solution. A lanthanide chelate, containing one 2,6-pyridylene and two 1,3-pyrazolylene groups, and having a covalent bond between the carbon and nitrogen atoms, has been synthesized (M. Alanso, J. de Mendoza, M. Remuiñan, H. Roman and J. C. Rodriguez-Ubis, 2nd *Conference on Methods and Applications of Fluorescence Spectroscopy*, Graz, Austria, 14–17.10.1991, P1/25). The luminescence properties of this chelate have not been published. The chelate has no group for coupling to biologically active material and it cannot be used as such for applications mentioned in this invention.

THE INVENTION

The compounds of this invention are lanthanide chelates comprising three heterocyclic rings covalently coupled to each other (either one 2,6-pyridylene and two five-membered unsaturated heterocyclic ring moieties or two 2,6-pyridylenes one five-membered unsaturated heterocyclic ring moiety) and two chelating groups so seated that they together chelate the same lanthanide ion even in aqueous solutions. Optionally, these lanthanide chelates also contain a reactive group for coupling to biologically active molecules.

The compounds of the invention are lanthanide chelates consisting of a Lanthanide ion and a chelator having a common structure shown in Formula I.

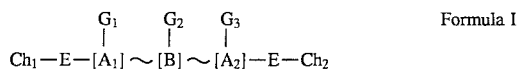

Formula I

The acid, ordinary salts and ester forms of Formula I are also novel and notable.

In Formula I, ~represents a covalent bond between two carbon atoms and—represents a covalent bond.

E represents methylene ($CH_2$) or carbonyl ($C=O$).

One or two of $[A_1]$, $[B]$ and $[A_2]$ in a $[A_1]$~$[B]$~$[A_2]$ structure represent a bivalent five-membered unsaturated heterocyclic ring. Each of the remaining of $[A_1]$, $[B]$ and $[A_2]$ is 2,6-pyridylene. Preferably either $[A_1]$ and $[A_2]$ or $[B]$ are 2,6-pyridylenes. The heteroatoms in five-membered unsaturated heterocyclic rings are selected from the group consisting of nitrogen, sulphur or oxygen. One heteroatom in each ring coordinates to the same lanthanide ion so that two five-membered rings are formed, in which one member is the lanthanide ion and two members are coordinating heteroatoms of different rings $[A_1]$, $[B]$ and $[A_2]$. Examples of preferable five-membered unsaturated heterocyclic bivalent groups include:

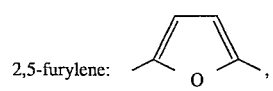
2,5-furylene:

2,4-thiazolylene:

2,5-thiazolylene:

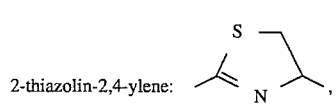
2-thiazolin-2,4-ylene:

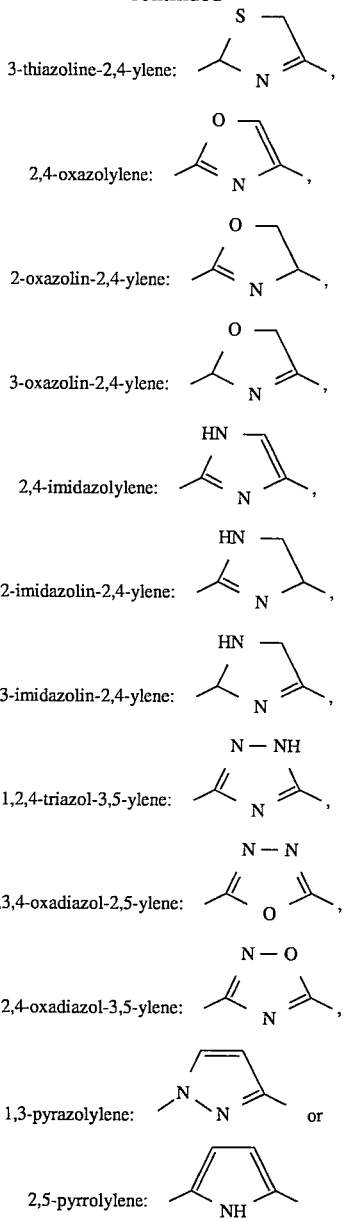

In 2,6-pyridylenes and in five-membered unsaturated heterocyclic bivalent rings, one hydrogen can be replaced with the appropriate group $G_1$, $G_2$ and $G_3$.

The substituents $G_1$, $G_2$ and $G_3$ can be selected from the group consisting of hydroxy, nitro, amino or lower alkyl substituted amino, lower aryl substituted amino or lower acyl substituted amino, alkyl, aryl, alkylaryl, arylalkyl, arylethynyl (such as phenylathynyl), alkoxy or aryloxy groups with the proviso that alkyls contain 1–12 carbon atoms and aryls are selected from phenyl, naphthyl and pyridyl. $G_1$, $G_2$ and $G_3$ can also be a group containing aryl (selected from phenyl, naphthyl and pyridyl) and alkylene parts that contain from 1 to 8 carbon atoms and additionally from 0 to 4 other atoms such as oxygen, sulphur, nitrogen or phosphorus. Each of the above mentioned groups optionally contains amino, aminooxy, carboxyl, hydroxy, aldehyde or mercapto groups or an activated form made from them, such as isothiocyanato, isocyanato, diazonium, bromoacetamido, iodoacetamido, reactive esters (such as N-hydroxysuccinimide, 4-nitrophenyl and 2,4-dinitrophenyl esters), pyridyl-2-dithio, 4-chloro-6-ethoxytriazon-2-ylamino or 4,6-dichlorotriazon-2-ylamino. Other examples of suitable groups to be used in the labelling of compounds exhibiting biological affinity are presented e.g. in R. F. Steiner and I. Weinryb (eds.), "*Excited States of Proteins and Nucleic Acids*", Basingstibe Corp., London, 1971 One or two of the substituents $G_1$, $G_2$ and $G_3$ can also be attached to a compound exhibiting biospecific affinity. Such molecules include e.g. proteins (such as enzymes), antibodies, antigens (haptens), oligo- and polynucleotides, lectins, receptors, carbohydrate structures (such as dextrans), protein A, IgG, drugs etc. This type of biologically active compounds are often called target substances (target molecules). The binding is performed in such a way that these molecules still retain their biospecific affinity.

$Ch_1$ and $Ch_2$ represent identical or different chelating groups, possibly linked together. Each of these chelating groups comprises at least two heteroatoms that are coordinated to the lanthanide ion and are selected from the group consisting of oxygen and nitrogen. At least one of the said coordinating heteroatoms in each of $Ch_1$ and $Ch_2$ forms a five- or six-membered ring together with the lanthanide ion and a coordinating heteroatom of one of $[A_1]$, $[B]$ and $[A_2]$. The distance between each pair of heteroatoms participating in the chelation and forming the same five or six-membered ring is two or three atoms, respectively.

Examples of efficient chelating heteroatoms include amino nitrogens (primary, secondary and tertiary amine) and negatively charged oxygens (carboxylate anions, enolate anions, phosphates and phosphonates). In most cases the bridge between the chelating heteroatoms contains 1, 2 or 3 saturated carbon atoms. Among particularly important $Ch_1$ and $Ch_2$ structures are N,N-bis(carboxymethyl)amino $[-N(CH_2COO^-)_2]$, N,N-bis(carboxyethyl)amino $[-N(CH_2CH_2COO^-)_2]$, analogous phosphates [e.g. $-N(CH_2-O-PO_3^{2-})_2$] and phosphonates [e.g. $-N(CH_2-PO_3^{2-})_2$] and 2,6-dicarboxypiperidin-1-yl. Alternatively, $Ch_1$ and $Ch_2$ may form one or two bridges that covalently connect the two outer heterocyclic rings ($[A_1]$ and $[A_2]$) giving a macrocyclic chelating compound. The bridge/bridges consist of saturated carbon, oxygen or nitrogen atoms. The nitrogens and the oxygen are selected from secondary or tertiary amino nitrogens and ether oxygens. Preferably, such a bridge together with the E—$[A_1]$—$[B]$—$[A_2]$—E system forms a carboxymethylated azacrown [the bridge is e.g. $-N(CH_2COO^-)CH_2CH_2N(CH_2COO^-)-$ or $-N(CH_2COO^-)-$], a cryptate [the bridge is e.g. $-N(CH_2CH_2-O-CH_2CH_2-O-CH_2CH_2)_2N-$] or a crown ether (the bridge is e.g. $-O-CH_2CH_2-O-CH_2-O-$ or $CH_2CH_2-O-$).

In some compounds of the invention the chelating heteroatoms (nitrogen and oxygen) may exist as the corresponding protonated forms and for oxygen also as ester forms, such as lower alkyl ($C_1-C_6$) benzyl or term-butyl esters From a spectrofluorometric point of view, the interesting chelate forms are molecules in which $Ch_1$ and $Ch_2$ together with E—$[A_1]$—$[B]$—$[A_2]$—E structure are chelated to the lanthanide ion, preferably to $Eu^{3+}$, $Tb^{3+}$, $Dy^{3+}$ or $Sm^{3+}$. These ligands can also be suitable for chelating such metal ions as $Ru^{2+}$, $Os^{2+}$, $Ir^{3+}$ and $Rh^{3+}$. As strong chelate forming compounds they are potential chelators also for radioactive isotopes of different metals to be used in classical applications for radiotracers.

The new chelates of our invention find applications in the areas that are classical for lanthanide chelates. Moreover, these compounds are useful as probes in time-resolved fluorescence microscopy, cytometry, nucleic acid sequencing, nucleic acid and protein finger printing, homogeneous hybridization assays for nucleic acid detection, homogeneous fluorometric immunoassays, multilabelling techniques and process controls in Industry.

In contrast to the many previously mentioned patents, the full coordination number of nine can easily be achieved with the new lanthanide chelates of this invention. This implies that there are no water molecules coordinated to the lanthanide ion. The quenching effect of water is thus minimized and the decay time of the luminescence is at its maximum. Thus the long-lived and very intensive luminescence of the lanthanide chelates can be effectively determined after the short-lived background has decayed. In e.g. microscopic applications and process controls in industry very stable (photo, thermodynamic ant kinetic stability) chelates are needed. As compared to the other known lanthanide chelate structures, these stability requirements are best fulfilled with the chelates of this invention.

The smaller size of unsaturated five-membered heterocycles compared to e.g. Pristine and phenol makes the ligands of this invention more flexible. This means that the lanthanide ion is better protected with the chelator and the pi-electrons of [$A_1$], [B] and [$A_2$] and the free electron pairs of their heteroatoms are better delocalized over [$A_1$]~[B]~[$A_2$].

The basicity of some five-membered unsaturated heterocycles (e.g. $pK_a$ for pyridine is 5.25 and for imidazole 6.953) makes them better chelators than pyridine. Moreover, in some of the chelates the aromatic structure is negatively charged (e.g. compounds containing 1,2,4-triazol-3,5-ylene). Not only does this stabilizes chelate, it additionally changes their adsorption properties diminishing unspecific binding to column materials and plastics.

It is known that C—H stretchings of the ligand decrease the luminescence intensity of the lanthanide chelates. The number of C—H bonds in the chelates of this invention has been reduced by five-membered heterocyclic ring moieties when compared with pyridines and phenols.

As compared with the lanthanide chelates these new structures of this invention exhibit a greater extinction coefficient, longer excitation wavelengths and better energy transfer from the ligand to the lanthanide ion, which lead to improvements in the detection sensitivity of the luminescent labels.

The structures and the synthetic routes employed in the experimental part are shown in reaction schemes 1–14. The compounds 42 (Scheme 7), 57a and 57b (Scheme 9), 68 (Scheme 10) and 80 are examples of compounds capable of binding to biologically active molecules. The other schemes represent the synthesis of potential structures which can easily be modified to such compounds with known methods.

E.g. compound 32, the corresponding 2,6-dicyanopyridine derivative and analogous compounds having a longer chain between the pyridine and the benzene rings can be used as a versatile starting material for chelates that can be coupled to compounds exhibiting biological affinity. In Example 84 compound 68 has been used for labelling of antibody. In Example 86 terbium(III) labelled antibody has been used for time-resolved fluorescence immunoassay and microscopy.

Modified iminodiacetic acid ester can be used instead of unsubstituted iminodiacetic acid ester as is taught in *Int. Pat. Appl.* PCT/SE89/00379 (1989).

General methods for the preparation of unsaturated five-membered heterocycles are state of the art (see the section Prior Art and e.g. A. R. Katritzky, "*Handbook of Heterocyclic Chemistry*", Pergamon Press, Great Britain, 1986).

The synthesis of phosphonic acids can be made using methods described in the literature, see e.g. E. K. Fields, *J. Am. Chem. Soc.* 74 (1952) 1525; G. R. Newkome, G. E. Kiefer, N. Matsumura and W. E. Puckett, *J. Org. Chem.* 50 (1985) 3807.

The new chelates of our invention can be used in time-resolved fluorescence immunoassays, DNA hybridization assays and microscopy analogously to the methods described in the literature, see e.g. I. A. Hemmilä, "Applications of Fluorescence in Immunoassays" in J. D. Winefordner and I. M. Kolthoff, Eds., *Chemical Analysis*, Vol 117, John Wiley & Sons, Inc., USA, 1991 and the references therein.

The method for the determination of an analyte in a sample comprises three steps: (a) contacting the sample with a reactant exhibiting biospecific affinity towards the analyte resulting in the formation of a complex comprising said analyte and said reactant, the condition and amounts of reactants being selected so that the amount of complex formed is a function of the amount of analyte in the sample, (b) quantitatively or qualitatively measuring the amount of complex formed by the use of a reactant that exhibits biospecific affinity for said complex and being labelled with an analytically detectable group and (c) relating the measured amount of the complex to the amount of analyte in the sample. The reactant labelled with the analytically detectable group complies with a lanthanide chelate according to this invention.

EXAMPLE 1

The synthesis of 2,6-bis{5'-[N,N-bis(methoxycarbonylmethyl) aminomethyl]-2'-furyl}-4-(2",4", 6"-trimethoxyphenyl)pyridine (1).

A mixture of 2,6-bis(2'-furyl)-4-(2"4"6"-trimethoxyphenyl)pyridine (0. 050 g, 0.13 mmol), dimethyl iminodiacetate (0.050 g, 0.32 mmol), 37% formaline (24 µl, 0.32 mmol) and

Scheme 1 The synthesis of compound 2

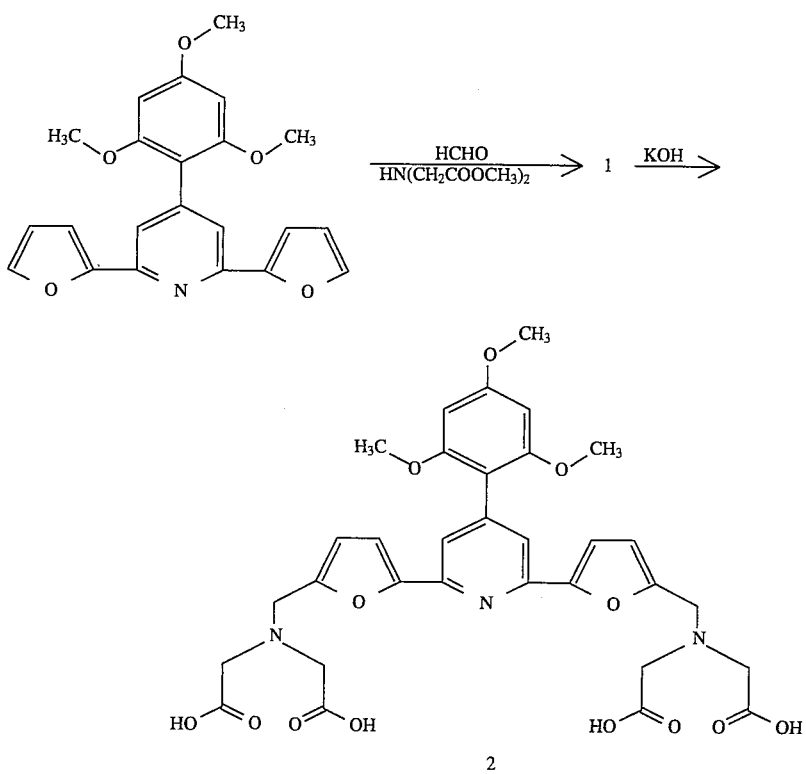

acetic acid (1 ml) was stirred for five hours at 110° C. After evaporation the residue was dissolved in dichloromethane, extracted with water and dried with sodium sulfate. The product was purified with flash chromatography (silica, chloroform). The yield was 11 mg (12%).

$^1$H NMR (60 MHz, CDCl$_3$): 3.60 (8H, s); 3.67 (12H, s); 3.74 (6H, s); 3.88 (3H, s); 4.03 (4H, s); 6.24 (2H, s); 6.39 (2H, d, J=3 Hz); 7.06 (2H, d, J=3 Hz); 7.50 (2H, s) UV ($\lambda_{max}$ in ethanol): 331 & 284 nm

EXAMPLE 2

The synthesis of 2,6-bis{5'-[N,N-bis(carboxymethyl aminomethyl]-2'-furyl}-4-(2", 4", 6"-trimethoxyphenyl)pyridine (2).

A mixture of compound 1 (11 mg, 15 umol) and 0.5M potassium hydroxide in ethanol (1 ml) was stirred for two hours. The solution was neutralized with 1M hydrochloric acid and evaporated to dryness. The residue was dissolved in water (0.5 ml). UV ($\lambda_{max}$ in water as free ligand): 331 & 283 nm UV ($\lambda_{max}$ in water as europium chelate): 338, 300 & 290 nm

EXAMPLE 3

The synthesis of 2,6-bis(4'-carboxy-2'-thiazolin2'-yl)pyridine (3).

L-Cysteine (0.66 g, 5.4 mmol) was dissolved in water (5 ml) and the solution was neutralized with sodium bicarbonate. A mixture of 2,6-dicyanopyridine (0.24 g, 1.9 mmol) in methanol (5 ml) was added to the solution of L-cysteine. After evaporation of methanol the crystallized product was filtered and washed with acetone. The yield was 0.35 g (55%).

$^1$H NMR (60 MHz, D$_2$O): 3.23–385 (4H m); 520 (2H, J=9 Hz); 8.05–8.35 (3H, m) UV ($\lambda_{max}$ in water as free ligand): 288 nm UV ($\lambda_{max}$ in water as europium(III) chelate: 295 & 240 nm

Scheme 2 The synthesis of compound 5

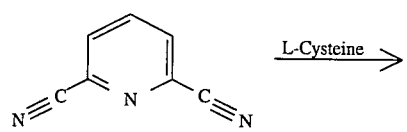

-continued
Scheme 2 The synthesis of compound 5

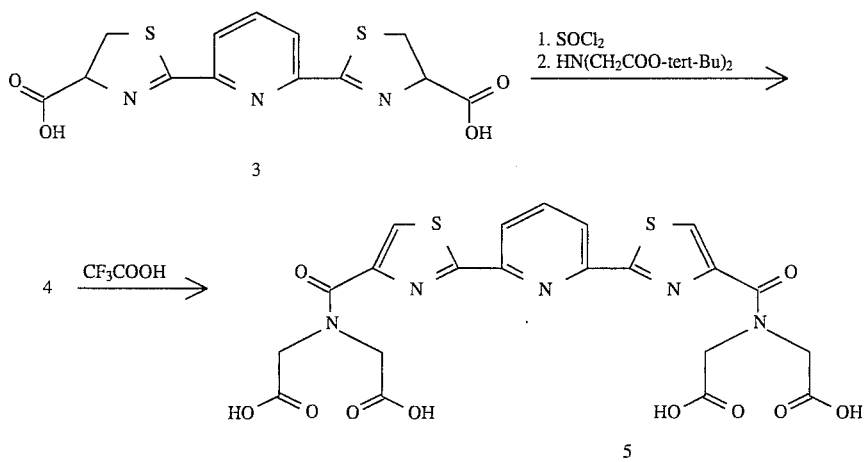

EXAMPLE 4

The synthesis of 2,6-bis{4'-[N,N-bis(tert-butoxycarbonylmethyl)aminocarbonyl]-2'-thiazolyl}pyridine (4).

A mixture of compound 3 (0.35 g, 1.0 mmol) and thionyl chloride (5 ml) was refluxed for one hour. After evaporation to dryness the residue was dissolved in dry pyridine (6 ml), di-tert-butyl iminodiacetate (0.64 g, 2.6 mmol) was added and the solution was refluxed for two hours. The solution was evaporated, dissolved in chloroform and filtered. The product was purified with flash chromatography (silica, chloroform).

$^1$H NMR (60 MHz, CDCl$_3$): 1.45 (18H, s); 1.51 (18H, s); 4.26 (4H, s); 4.63 (4H, s); 7.86–8.27 (3H, m); 8.33 (2H, s) UV ($\lambda_{max}$ in ethanol): 326 & 289 nm; mol wt (MS): 787 (M$^+$)

EXAMPLE 5

The synthesis of 2,6-bis{4'-[N,N-bis(carboxymethyl)aminocarbonyl]-2'-thiazolyl}pyridine (5).

A solution of compound 4 in trifluoroacetic acid was kept at room temperature overnight. After evaporation the residue was triturated with diethyl ether and filtered.

$^1$H NMR (60 MHz, DMSO-d$_6$): 4.21 (4H, s); 4.57 (4H, s); 8.10–8.30 (3H, m); 8.50 (2H, s) UV ($\lambda_{max}$ in water as free ligand): 325 & 278 nm UV ($\lambda_{max}$ in water as europium(III) chelate): 325 & 278 nm

EXAMPLE 6

The synthesis of 2,6-bis(5'-methyl-4'-phenylthiazol-2'-yl)pyridine (6).

A mixture of 2,6-pyridinedithiodicarboxamide (0.76 g, 2.9 mmol), 2-bromo-1-phenyl-1-propanone (1.8 g, 8.4mmol), ethanol (14 ml) and N,N-dimethylformamide (5 ml) was refluxed for 8.5 hours. Solid material was filtered and washed with ethanol. The suspension of the hydrobromic salt of the produce in hot water (40 ml) was alkalized with 20 sodium bicarbonate Scheme 3. The synthesis of compound 9

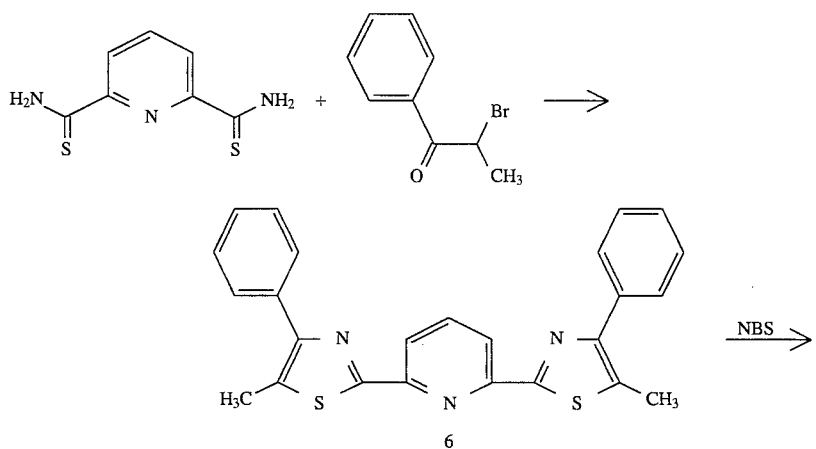

-continued
Scheme 3. The synthesis of compound 9

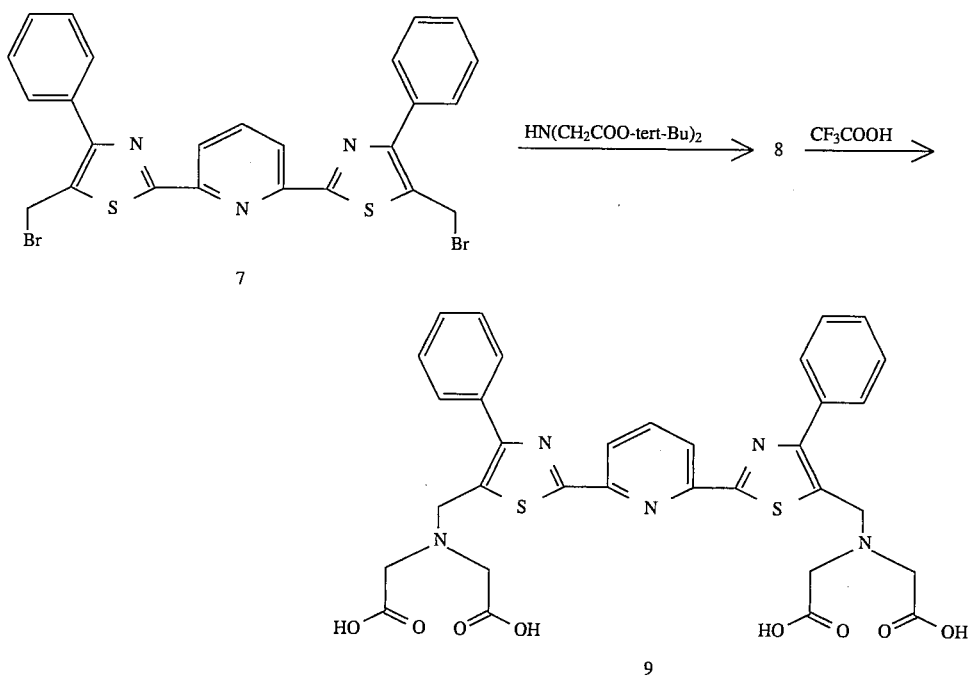

solution. The product was filtered and washed with water. The yield was 1.35 g (81%). M.p. 273° C.

$^1$H NMR (400 MHz, CDCl$_3$): 2.67 (6H, s); 7.36–7.40 (2H, m); 7.47–7.50 (4H, m); 7.74–7.76 (4H, m); 7.86 (1H, t, J=7.7 Hz); 8.21 (2H, d, J=7.7 Hz) UV ($\lambda_{max}$ in acetonitrile): 342 & 238 nm

EXAMPLE 7

The synthesis of 2,6-bis(5'-bromomethyl-4'-phenylthiazol-2'-yl)pyridine (7).

A mixture of compound 6 (0,50 g, 1.2 mmol), N-bromosuccinimide (0.42 g, 2.4 mmol), α,α'-azoisobutyronitrile (21 mg, 0.13 mmol) and benzene (140 ml) was refluxed for six hours. The reaction mixture was evaporated and the product was purified with flash chromatography (silica, dichloromethane). The yield was 0.10 g (15%). M.p. 223° C.

$^1$H NMR (400 MHz, CDCl$_3$): 4.88 (4H, s); 7.45–7.48 (2H, m); 7.52–7.56 (4H, m); 7.82–7.85 (4H, m); 7.91 (1H, t, J=7.8 Hz); 8.29 (2H, d, J=7.8 Hz) UV ($\lambda_{max}$ in ethanol): 340, 316 & 243 nm

EXAMPLE 8

The synthesis of 2,6-bis{5'-[N,N-bis(tert-butoxycarbonylmethyl)aminomethyl]-4'-phenylthiazol-2'-yl}-pyridine (8).

A mixture of compound 7 (90 mg, 0.15 mmol), di-tert-butyl iminodiacetate (76 mg, 0.31 mmol), dry potassium carbonate (0.21 g, 1.5 mmol) and dry acetonitrile (30 ml) was refluxed for six hours. The reaction mixture was filtered and the filtrate was evaporated to dryness. The residue was dissolved in chloroform (5 ml), washed with water (2×2 ml) and dried with sodium sulfate. Evaporation left a pure product. The yield was 0.14 g (100%). M.p. 121°–123° C.

$^1$H NMR (400 MHz, CDCl$_3$): 1.43 (36H, s); 3.54 (8H, s); 4.30 (4H, s); 7.35–7.39 (2H, m); 7.44–7.47 (4H, m); 7.72–7.74 (4H, m); 7.86 (1H, t, J=7.8 Hz); 8.26 (2H, d, J=7.8 Hz) UV ($\lambda_{max}$ in ethanol): 340, 312 & 239 nm

EXAMPLE 9

The synthesis of 2,6-bis{5'-[N,N-bis(carboxymethyl)aminomethyl]-4'-phenylthiazol-2'-yl}-pyridine (9).

A solution of compound 8 (100 mg, 0.11 mmol) in trifluoroacetic acid (2 ml) was kept 1.5 hours at room temperature. After evaporation the residue was triturated with diethyl ether and filtered. The yield was 30 mg (40%). M.p. 185° C. (dec.).

$^1$H NMR (400 MHz, DMSO-d$_6$): 3.56 (8H, s); 4.29 (4H, s); 7.42–7.45 (2H, m); 7.49–7.53 (4H, m); 7.72–7.74 (4H, m); 8.13 (1H, t, J=7.9 Hz); 8.26 (2H, d, J=7.9 Hz) UV ($\lambda_{max}$ in water as free ligand): 340, 305 & 237 nm UV ($\lambda_{max}$ in water as europium(III) chelate): 350, 310 & 240 nm Scheme 4.
The synthesis of compounds 14 and 16

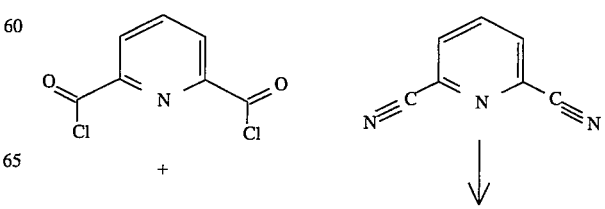

13
-continued
Scheme 4.
The synthesis of compounds 14 and 16

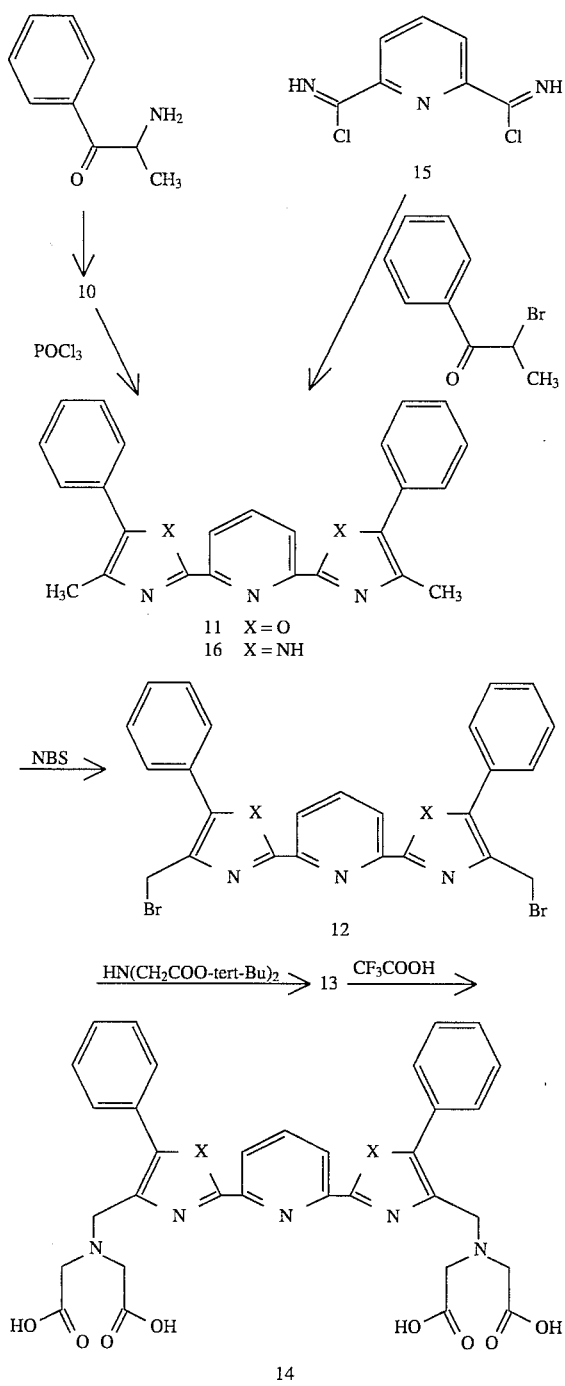

EXAMPLE 10

The synthesis of 2,6-bis[N-(1'-phenyl-1'-propanon-2'-yl) aminocarbonyl]pyridine (10).

2-Amino-1-phenyl-1-propanone hydrochloride (1.93 g, 10.3 mmol) was added in small portions to a mixture of 2,6-pyridinedicarbonyl dichloride (1.05 g, 5.20 mmol) and pyridine (25 ml). After refluxing for 15 min the reaction mixture was evaporated to dryness. The residue was dissolved in chloroform (50 ml), washed with saturated sodium bicarbonate (20 ml) and dried with sodium sulfate. The product was purified with flash chromatography (silica, petroleum ether/ethyl acetate, 1/1).

The yield was 1.60 g (72%). M.p. 71° C.

$^1$H NMR (400 MHz, CDCl$_3$): 1.65 (3H, d, J=7.3 Hz); 1.66 (3H, d, J=7.3 Hz); 5.79 (1H, quintet, J=7.3 Hz); 5.80 (1H, quintet, J=7.3 Hz); 7.55 (4H, t, J=7.4 Hz); 7.65 (2H, t, J=7.4 Hz); 8.06 (1H, t, J=7.8 Hz); 8.11–8.14 (4H, m); 8.39 (1H, d, J=7.8 Hz); 8.39 (1H, d, J=7.8 Hz); 8.94 (1 H, d, J=7.3 Hz); 9.02 (1H, d, J=7.3 Hz) UV ($\lambda_{max}$ in ethanol): 244 nm

EXAMPLE 11

The synthesis of 2,6-bis(4'-methyl-5'-phenyloxazol-2'-yl)pyridine (11).

A mixture of compound 10 (1.56 g, 3.65 mmol) and phosphorus oxychloride (55 ml) was refluxed for 23 hours. After evaporation to dryness the residue was treated with water and the mixture was neutralized with 1M sodium hydroxide. The crude product was filtered, washed with water and finally purified with flash chromatography (silica, 5% methanol in chloroform). The yield was 1.26 g (88%). M.p. 161°–163° C.

$^1$H NMR (400 MHz, CDCl$_3$): 2.56 (6H, s); 7.37 (2H, d, J=7.6 Hz); 7.49 (4H, t, J=7.6 Hz); 7.80 (4H, d, J=7.6 Hz); 7.95 (1H, t, J=8.0 Hz); 8.20 (2H, d, J=8.0 Hz) UV ($\lambda_{max}$ in ethanol): 350, 295 260 & 220(sh) nm

EXAMPLE 12

The synthesis of 2,6-bis(4'-bromomethyl-5'-phenyloxazol-2'-yl)pyridine (12).

A mixture of compound 11 (0.63 g, 1.6 mmol), N-bromosuccinimide (0.57 g, 3.2 mmol), α,α'-azoisobutyronitrile (29 mg, 0.18 mmol) and carbon tetrachloride (10 ml) was refluxed for three hours. After evaporation the solid material was washed several times with a mixture of petroleum ether and ethyl acetate (5/3). The yield was 0.44 g (50%). M.p. 234°–237° C.

$^1$H NMR (400 MHz, CDCl$_3$): 4.71 (4H, s); 7.46 (2H, t, J=7.3 Hz); 7.55 (4H, t, J=7.3 Hz); 7.88 (4H, d, J=7.3 Hz); 8.00 (1H, t, J=7.9 Hz); 8.28 (2H, d, J=7.9 Hz) UV ($\lambda_{max}$ in ethanol): 353, 293 & 262 nm

EXAMPLE 13

The synthesis of 2,6-bis{4'- [N,N-bis(tert-butoxycarbonylmethyl)aminomethyl ]-5'-phenyloxazol-2'-yl}pyridine (13).

A mixture of compound 12 (0.28 g, 0.50 mmol), di-tert-butyl iminodiacetate (0.25 g, 1.0 mmol), dry potassium carbonate (0.69 g, 5.0 mmol) and dry acetonitrile (50 ml) was refluxed overnight. The reaction mixture was filtered and the filtrate was evaporated to dryness. The residue was dissolved in chloroform (15 ml), washed with water (2×5 ml) and dried with sodium sulfate. The product was purified with flash chromatography (silica, petroleum ether/ethyl acetate, first 5/1 then 5/2). The yield of an oily product was 0.21 g (61%).

$^1$H NMR (400 MHz, CDCl$_3$): 1.43 (36H, s); 3.58 (8H, s); 4.21 (4H, s); 7.38 (2H, t, J=7.6 Hz); 7.49 (4H, t, J=7.6 Hz); 7.94 (1H, t, J=7.8 Hz); 8.01 (4H, d, J=7.6 Hz); 8.28 (2H, d, J=7.8 UV ($\lambda_{max}$ in ethanol): 335(sh), 301 & 262 nm

EXAMPLE 14

The synthesis of 2,6-bis{4'-[N,N-bis(carboxymethyl) aminomethyl]-5'-phenyloxazol-2'-yl}pyridine (14).

A solution of compound 13 (0.21 g, 0.24 mmol) in trifluoroacetic acetic acid (6.5 ml) was kept 1.5 hours at room temperature. After evaporation the residue was triturated with diethyl ether and filtered. The yield was 0.13 g (81%). M.p. 173° C. (dec.).

$^1$H NMR (400 MHz, DMSO-$d_6$): 3.65 (8H, s); 4.18 (4H, s); 7.47 (2H, t, J=7.8 Hz); 7.56 (4H, t, J=7.8 Hz); 8.01 (4H, d, J=7.8 Hz); 8.19–8.23 (1H, m); 8.28–8.30 (2H, m) UV ($\lambda_{max}$ in water as free ligand): 332, 310 & 259 nm UV ($\lambda_{max}$ in water as europium(III) chelate): 350 & 243 nm

EXAMPLE 15

The synthesis of 2,6-pyridinedicarboxyamidine dihydrochloride (15).

A mixture of 2,6-dicyanopyridine (7.0 g, 54 mmol), sodium methoxide (0.59 g, 11 mmol) and methanol (50 ml) was stirred for 2.5 hours at room temperature. Ammonium chloride (5.9 g, 110 mmol) was added and the reaction mixture was stirred for three days. The product was filtered and washed with diethyl ether. The yield was 12.0 g (94%). M.p. >310° C. (dec.).

$^1$H NMR (400 MHz, D$_2$O): 8.32–8.49 (3H, m) UV ($\lambda_{max}$ in water): 273 & 224 nm

EXAMPLE 16

The synthesis of 2,6-bis(4'-methyl-5'-phenylimidazol-2'-yl)pyridine (16).

0.5M Potassium hydroxide (17 ml) was added to a mixture of compound 15 (0.50 g, 2.1 mmol), 2-bromo-1-phenyl-1-propanone (0.89 g 4.2 mmol) N,N-diisopropylethylamine (1.1 g, 8.4 mmol) and chloroform (10 ml). After refluxing for one day the solid material was filtered, washed with chloroform and the filtrate was evaporated to dryness. The product was purified with flash chromatography (silica, first chloroform, then 5% methanol in chloroform). The yield of an oily product was 0.17 g (21%).

$^1$H NMR (400 MHz, CDCl$_3$): 2.28 (6H, s); 7.21 (2H, t, J=7.3 Hz); 7.30 (4H, t, J=7.3 Hz); 7.49–7.52 (4H, m); 7.67 H, t, J=7.8 Hz); 8.05 (2H, d, J=7.8 Hz) UV ($\lambda_{max}$ in ethanol): 353, 306 & 266 nm mol wt (MS): 391 (M$^+$)

Scheme 5.
The synthesis of compound 18

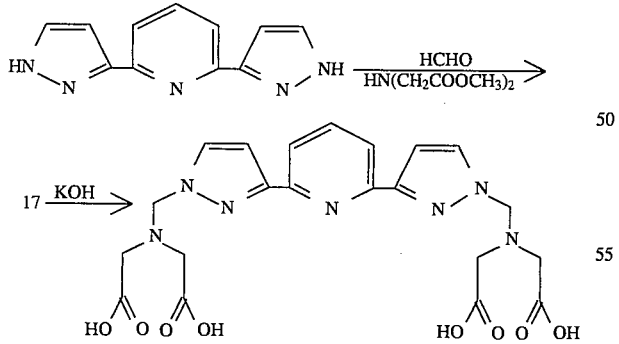

EXAMPLE 17

The synthesis of 2,6-bis{1'-N,N-bis(methoxycarbonylmethyl)aminomethyl]-3'-pyrazolyl}pyridine (17).

A mixture of 37% formaline (0.8 g, 10 mmol), methanol (40 ml) and dimethyl iminodiacetate (1.6 g, 10 mmol) was evaporated to dryness. The residue was dissolved in methanol (40 ml) and evaporated once again. 2,6-Bis(3'-pyrazolyl)pyridine (1.1 g, 5.0 mmol) was added and the reaction mixture was stirred for 20 hours at 110° C. The product was purified with flash chromatography (silica, triethylamine/petroleum ether/ethyl acetate, 1/5/3). The yield was 1.54 g (55%).

$^1$H NMR (60 MHz, CDCl$_3$): 3.67 (12H, s); 3.67 (8H, s); 5.20 (4H, s); 7.06 (2H, d, J=2 Hz); 7.61 (2H, d, J=2 Hz); 7.74–8.02 (3H, m) mol wt (MS): 557 (M$^+$) UV ($\lambda_{max}$ in ethanol): 301 & 251 nm

EXAMPLE 18

The synthesis of 2,6-bis{1'-[N,N-bis(carboxymethyl)aminomethyl]-3'-pyrazolyl}pyridine (18).

A mixture of compound 17 (1.0 g, 1.8 mmol), 0.5M potassium hydroxide in ethanol (50 ml) was stirred for three hours, water (0.5 ml) was added and the reaction mixture was stirred for one hour. The reaction mixture was evaporated to dryness and the residue was dissolved in water (2 ml). The solution was acidified with 2M hydrochloric acid and triturated with ethanol. The solid material was filtered, washed with ethanol and the filtrate was evaporated to dryness. The product was purified with flash chromatography (silica, acetonitrile/water, 4/1). After evaporation the product was crystallized from water. The yield was 0.19 g (21%).

$^1$H NMR (60 MHz, DMSO-$d_6$): 3.64 (8H, s); 5.46 (4H, s); 6.97–7.05 (2H, m); 7.75–7.92 (5H, m) UV ($\lambda_{max}$ in water as free ligand): 301 & 234 nm UV ($\lambda_{max}$ in water as europium(III) chelate): 313, 263, 254 & 234 nm

Scheme 6. The synthesis of compounds 23, 30 and 39

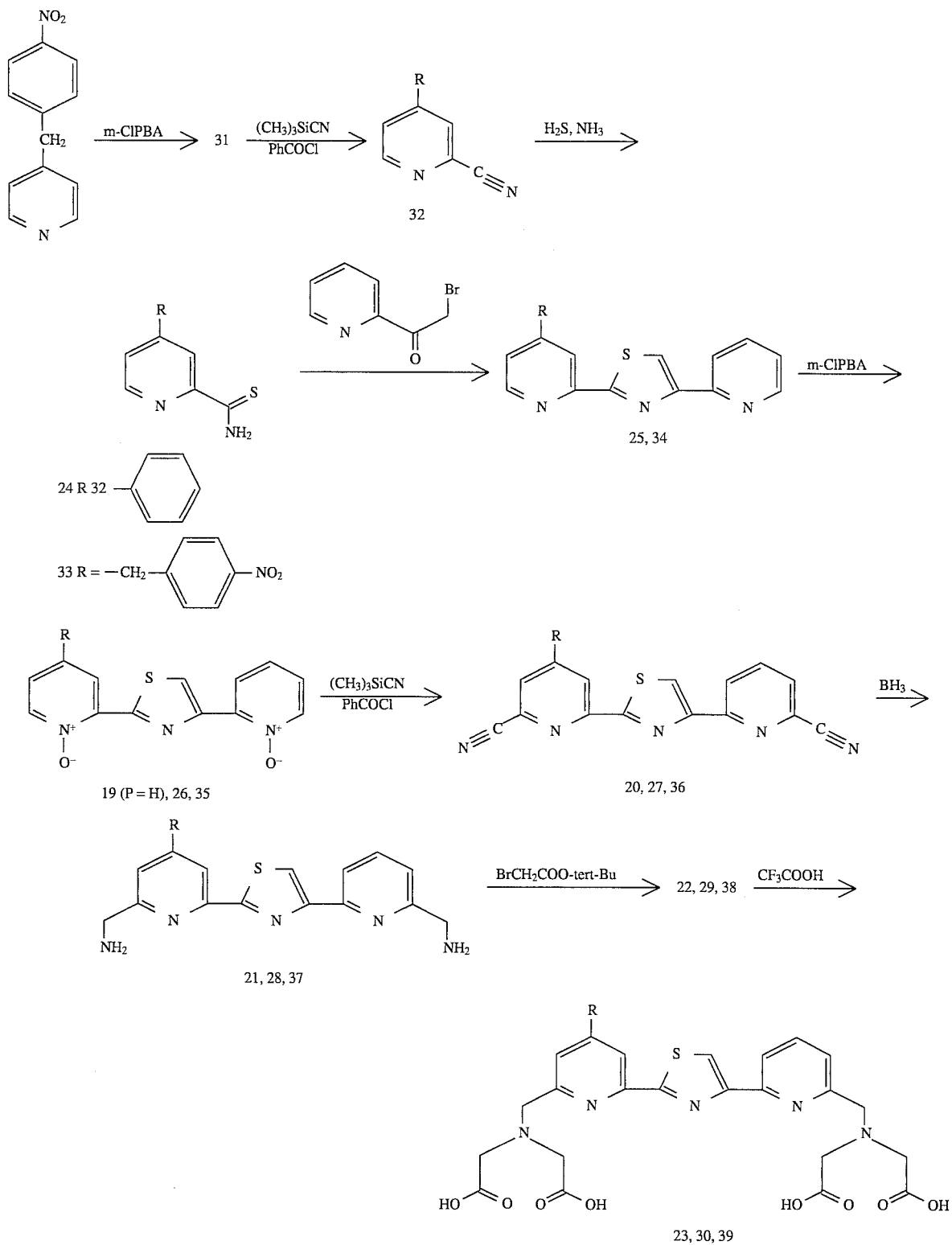

EXAMPLE 19

The synthesis of 2,4di(2'-pyridyl)thiazole N',N'-dioxide (19).

m-Chloroperbenzoic acid (50–55%, 25.9 g, about 75 mmol) was added in small portions during 24 hours to a mixture of 2,4-di(2'-pyridyl)thiazole (2.39 g, 10.0 mmol) and dichloromethane (400 ml). After stirring for 24 hours, the reaction mixture was washed with 10% sodium carbonate (3×150 ml) and water (150 ml). The combined water fractions were extracted with chloroform (150 ml). The combined organic fractions were dried with sodium sulfate and evaporated to dryness. The yield was 2.71 g (100%).

$^1$H NMR (60 MHz, CDCl$_3$): 7.18–7.66 (4H, m); 7.87–8.04 (1H, m); 8.35–8.76 (3H, m); 9.53 (1H, s) mol wt (MS): 271 (M$^+$) UV ($\lambda_{max}$ in ethanol): 324 & 249 nm

EXAMPLE 20

The synthesis of 2,4-bis(6'-cyano-2'-pyridyl)thiazole (20).

Trimethylsilylcyanide (20 ml, 150 mmol) was added during five minutes to a mixture of compound 19 (2.71 g, 10.0 mmol) and dichloromethane (110 ml). After stirring for five minutes benzoyl chloride (7.2 ml, 60 mmol) was added and the reaction mixture was stirred for 9 days. After concentration to half of its original volume, 10% potassium carbonate (300 ml) was added and the reaction mixture was stirred for half an hour. The product was filtered, washed with water and cold dichloromethane. The yield was I. 84 g (64% ). mol wt (MS): 289 (M$^+$) UV ($\lambda_{max}$ in ethanol): 301, 271 & 252 nm

EXAMPLE 21

The synthesis of 2,4-bis(6'-aminomethyl-2'-pyridyl)thiazole pentahydrochloride (21).

1M Borane in tetrahydrofuran (52 ml, 52 mmol) was added during 10 minutes to a mixture of compound 20 (1.16 g, 4.00 mmol) and dry tetrahydrofuran (50 ml). After stirring for 24 hours, the extra borane was destroyed by adding methanol. The mixture was evaporated to dryness and methanol saturated with hydrogen chloride (70 ml) was added. After stirring for one hour, the product was filtered and washed with cold methanol The yield was 0.80 g (42%).

$^1$H NMR (60 MHz, D$_2$O): 4.56 (2H, s); 4.57 (2H, s); 7.55–7.72 (2H, m); 8.00–8.47 (4H, m); 8.56 (1H, s) UV ($\lambda_{max}$ in water): 320 (sh), 292 & 244 nm

EXAMPLE 22

The synthesis of 2,4-bis{6'-bis[N,N-bis(tert-butoxycarbonylmethyl)aminomethyl]-2'-pyridyl}thiazole (22).

A mixture of compound 21 (0.48 g, 1.0 mmol), N,N-diisopropylethylamine (2.6 ml, 15 mmol), tert-butyl bromoacetate (0.78 g, 4.0 mmol) and acetonitrile (20 ml) was refluxed for 23 hours. After evaporation, the residue was dissolved in chloroform (50 ml), washed with water (3×20 ml) and dried with sodium sulfate. The product was purified with flash chromatography (silica, petroleum ether/ethyl acetate, 5/3.). The yield was 0.47 g (63%).

$^1$H NMR (400 MHz, CDCl$_3$): 1.48 (18H, s); 1.48 (18H, s); 3.55 (8H, s); 4.11 (2H, s); 4.12 (2H, s); 7.59 (1H, d, J=7.6 Hz); 7.71 (1H; d, J=7.6 Hz); 7.79 (1H, t, J=7.6 Hz); 7.81 (1H, t, J=7.6 Hz); 8.13 (1H, d, J=7.6 Hz); 8.18 (1H, d, J=7.6 Hz); 8.20 (1H, s) mol wt (MS): 753 (M$^+$)

EXAMPLE 23

The synthesis of 2,4-bis{6'-bis[N,N-bis(carboxymethyl)aminomethyl]-2'-pyridyl}thiazole (23).

This compound (23) was synthesized using a method analogous to the synthesis described in Example 9. The yield was 100%.

$^1$H NMR (400 MHz, DMSO-d$_6$): 3 63 (4H, s); 3.72 (4H, s); 4.12 (2H, s); 4.21 (2H, s); 7.56 (1H, d, J=7.6 Hz); 7.69 (1H, d, J=7.6 Hz); 7.99 (1H, t, J=7.6 Hz); 8.03 (1H, t, J=7.6 Hz); 8.14 (1H, d, J=7.6 Hz); 8.18 (1H, d, J=7.6 Hz); 8.39 (1H, s) UV ($\lambda_{max}$ in water as free ligand): 325(sh), 294 & 247 nm UV ($\lambda_{max}$ in water as europium(III) chelate): 331, 295 & 243 nm

EXAMPLE 24

The synthesis of 4-phenylpyridine-2-tiocarboxamide (24).

Absolute ethanol saturated with ammonia (10 ml ) was added to a cold solution of 2-cyano-4-phenylpyridine (1.8 g, 10 mmol) and absolute ethanol (30 ml). The mixture was saturated with hydrogen sulfide. After stirring overnight, the solution was concentrated to 10 ml. The cold mixture was filtered and washed with cold ethanol. The yield was 1.69 g (79%).

$^1$H NMR (60 MHz, CDCl$_3$): 7.69–7.94 (6H, m); 8.83 (1H, d, J=5 Hz); 9.24 (1H, d, J=2 Hz) UV ($\lambda_{max}$ in ethanol): 322 & 241 nm

EXAMPLE 25

The synthesis of 2-(4'-phenyl-2'-pyridyl)-4-(2"-pyridyl)thiazole (25).

A mixture of compound 24 (1.07 g, 5.00mmol), 2-(bromoacetyl)pyridine (1.00 g, 5.00 mmol) and ethanol (20 ml) was refluxed for three hours. A cold mixture was filtered and washed with cold ethanol. The suspension of the hydrobromic salt of the product in hot water (40 ml) was alkalized with solid sodium carbonate. The product was filtered and washed with cold water. The yield was 1.25 g (79%).

$^1$H NMR (400 MHz, CDCl$_3$): 7.25–7.29 (1H, m); 7.47–7.51 (1H, m); 7.52–7.58 (3H, m); 7.76–7.79 (2H, m); 7.80–7.85 (1H, dt, J=2 & 8 Hz); 8.23 (1H, s); 8.30 (1H, d, J=8 Hz); 8.57 (1H, d); 8.65–8.69 (2H, m) UV ($\lambda_{max}$ in ethanol): 320, 282(sh) & 249 nm

EXAMPLE 26

The synthesis of 2-(4'-phenyl-2'-pyridyl)-4-(2"-pyridyl)thiazole N',N"-dioxide (26)

This compound (26) was synthesized using a method analogous to the synthesis described in Example 19. The yield was 93%.

$^1$H NMR (400 MHz, CDCl$_3$): 7.23–7.27 (1H, m); 7.41–7.46 (1H, m); 7.48–7.52 (1H, m); 7.55–7.60 (3H, m); 7.74–7.77 (2H, m); 8.41 (1H, d); 8.45 (1H, d); 8.69 (1H, dd); 8.90 (1H, d); 9.58 (1H, s)

EXAMPLE 27

The synthesis of 2-(6'-cyano-4'-phenyl-2'-pyridyl)-4-(6"-cyano-2"-pyridyl)thiazole (27).

This compound (27) was synthesized using a method analogous to the synthesis described in Example 20. The yield was 65%.

$^1$H NMR (400 MHz, DMSO-d$_6$): 7.50 (1H, t, J=8 Hz); 7.58–7.67 (2H, m); 7.95 (1H, d, J=8 Hz); 8.04–8.08 (2H, m); 8,24 (1H, t, J=8 Hz); 8.60 (1H, d, J=1 Hz); 8.67 (1H, d, J=8 Hz); 8.70 (1H, s); 8.83 (1H, d, J=1 Hz)

EXAMPLE 28

The synthesis of 2-(6'-aminomethyl-4'-phenyl-2'pyridyl)-4-(6"-aminomethyl-2"-pyridyl)thiazole pentahydrochloride (28).

This compound (28) was synthesized using a method analogous to the synthesis described in Example 2. The yield was 71%. UV ($\lambda_{max}$ in ethanol): 318 & 251 nm

EXAMPLE 29

The synthesis of 2-{6'-N,N-bis(tert-butoxycarbonylmethyl)aminomethyl]-4'-phenyl-2'-pyridyl}-4- {6"- [N,N-bis-(tert-butoxycarbonylmethyl)aminomethyl]-2"-pyridyl}-thiazole (29).

This compound (29) was synthesized using a method analogous to the synthesis described in Example 22. The yield was 89%.

$^1$H NMR (60 MHz, CDCl$_3$): 1.47 (36H, s); 3.54 (4H, s); 3.58 (4H, s); 3.95 (2H, s); 4.18 (2H, s); 7.42–7.94 (8H, m); 8.11 (1H, d, J=2 Hz); 8.20 (1H, s); 8.43 (1H, d, J=2 Hz)

EXAMPLE 30

The synthesis of 2-{6'-[N,N-bis(carboxymethyl)aminomethyl]4'-phenyl-2'-pyridyl}-4-{6"-[N,N-bis(carboxymethyl)aminomethyl]-2"-pyridyl}thiazole (30).

This compound (30) was synthesized using a method analogous to the synthesis described in Example 9. The yield was 91%.

$^1$H NMR (60 MHz, DMSO-d$_6$): 3.67 (4H, s); 3.73 (4H, s); 4.21 (4H, s); 7.47–7.72 (4H, m); 7.77–8.25 (5H, m); 8.40–8.49 (2H, m) UV ($\lambda_{max}$ in water as free ligand): 331 (sh) & 252 nm UV ($\lambda_{max}$ in water as europium(III) chelate): 334, 288 & 251 nm

EXAMPLE 31

The synthesis of 4-(p-nitrobenzyl)pyridine N-oxide (31).

m-Chloroperbenzoic acid (50–55%, 74.7 g, about 190 mmol) was added to a cold mixture of 4-(p-nitrobenzyl)pyridine (21.4 g, 100 mmol) and dichloromethane (250 ml). After stirring for two hours, water (200 ml) was added and the reaction mixture was alkalized with solid sodium carbonate. Fractions were separated and the water fraction was extracted with a mixture of ethanol and chloroform (4×150, ½). The combined organic fractions were dried with sodium sulfate. The yield was 19.1 g (83%).

$^1$H NMR (60 MHz, CDCl$_3$): 4.07 (2H, s); 7.08 (2H, d, J=7 Hz); 7.35 (2H, d, J=9 Hz); 8.17 (2H, d, J=7 Hz); 8.22 (2H, d, J=9 Hz) UV ($\lambda_{max}$ in ethanol ): 273 nm

EXAMPLE 32

The synthesis of 2-cyano-4-(p-nitrobenzyl)pyridine (32).

Trimethylsilylcyanide (50 ml, 400 mmol) was added to a mixture of compound 31 (18.2 g, 79.0 mmol) and dichloromethane (160 ml). After stirring for five minutes, benzoyl chloride (20 ml, 160 mmol) was added and the reaction mixture was stirred for half an hour. Water (160 ml) and solid potassium carbonate (50 g) was added and the reaction mixture was stirred for half an hour. Fractions were separated and the water fraction was extracted with dichloromethane (2×100 ml ). The organic fractions were 1 dried with sodium sulfate and the product was crystallized from toluene. The yield was 10.0 g (53%).

$^1$H NMR (60 MHz, CDCl$_3$): 4.14 (2H, s); 7.32 (1H, d, J=5 Hz); 7.33 (2H, d, J=9 Hz); 7.48 (1H, s); 8.23 (2H, d, J=9 Hz); 8.64 (1H, d, J=5 Hz) UV ($\lambda_{max}$ in ethanol): 266 nm

EXAMPLE 33

The synthesis of 4-(p-nitrobenzyl)pyridine-2-tiocarboxamide (33).

Absolute ethanol saturated with ammonia (20 ml) was added to a cold mixture of compound 32 (4.8 g, 20 mmol), absolute ethanol (100 ml) and dichloromethane (80 ml). The mixture was saturated with hydrogen sulfide. After stirring overnight, the solution was concentrated. The cold mixture was filtered and wasted with cold ethanol. A suspension of the solid material in chloroform (100 ml) was filtered, washed with chloroform and the filtrate was evaporated to dryness. The yield was 3.3 g (60% ).

$^1$H NMR (60 MHz, CDCl$_3$): 4.17 (2H, s); 7.19 (1H, dd, J=1 & 5 Hz); 7.35 (2H, d, J=8 Hz); 8.19 (2H, d, J=8 Hz); 8.44 (2H, d, J=5 Hz); 8.60 (1H, d, J=1 Hz) mol wt (MS): 273 (M$^+$) UV ($\lambda_{max}$ in ethanol): 317 & 271 nm

EXAMPLE 34

The synthesis of 2-[4'-(p-nitrobenzyl)-2'-pyridyl]-4-(2"-pyridyl) thiazole (34).

This compound (34) was synthesized using a method analogous to the synthesis described in Example 25. The yield was 61% after a crystallization from methanol.

$^1$H NMR (60 MHz, CDCl$_3$): 4.20 (2H, s); 7.11–7.50 (4H, m); 7.69–8.31 (6H, m); 8.55–8.71 (2H, m) UV ($\lambda_{max}$ in ethanol): 315(sh), 285 & 246 nm

EXAMPLE 35

The synthesis of 2-[4'-(p-nitrobenzyl)-2'-pyridyl]-4-2"-pyridyl)thiazole N',N"-dioxide (35).

This compound (35) was synthesized using a method analogous to the synthesis described in Example 19. The yield was 82%.

$^1$H NMR (60 MHz, DMSO-d$_6$): 4.32 (2H, s); 7.33–7.55 (4H, m); 7.72–7.89 (4H, m); 8.13–8.69 (4H, m) UV ($\lambda_{max}$ in ethanol): 326 & 253 nm

EXAMPLE 36

The synthesis of 2-[6'-cyano-4'-(p-nitrobenzyl)-2'-pyridyl]-4-(6"-cyano-2"-pyridyl)thiazole (36).

This compound (36) was synthesized using a method analogous to the synthesis described in Example 20. After the addition of 10% potassium carbonate, the mixture was extracted several times with chloroform. The combined organic fractions were dried with sodium sulfate. The yield was 69%.

$^1$H NMR (60 MHz, CDCl$_3$): 4.21 (2H, s) 7.27–7.60 (5H, m); 7.81–8.20 (4H, m); 8.33 (1H, s)

EXAMPLE 37

The synthesis of 2-[6'-aminomethyl-4'-(p-nitrobenzyl)-2'-pyridyl]-4-(6"-aminomethyl-2"-pyridyl)thiazole pentahydrochloride (37).

This compound (37) was synthesized using a method analogous to the synthesis described in Example 21. After the addition of methanol saturated with hydrogen chloride and stirring for one hour, the solution was evaporated to dryness. The residue was triturated with cold tetrahydrofuran and filtered. The yield was 63%. UV ($\lambda_{max}$ in water): 315(sh), 284 & 242 nm

EXAMPLE 38

The synthesis of 2-{6'-[N,N-bis(tert-butoxycarbonylmethyl)aminomethyl]-4'-(p-nitrobenzyl)-2'-pyridyl}-4 {6"-[N,N-bis(tert-butoxycarbonylmethyl)aminomethyl]-2"-pyridyl}thiazole (38).

This compound (38) was synthesized using a method analogous to the synthesis described in Example 22. The product was purified with flash chromatography (silica, petroleum ether/ethyl acetate, 5/2). The yield was 24%.

$^1$H NMR (60 MHz, CDCl$_3$): 1.46 (36H, s); 3.52 (8H, s); 3.80 (2H, s); 3.95 (2H, s); 4.08 (2H, s); 7.17–8.17 (10H, m)

EXAMPLE 39

The synthesis of 2-{6'-[N,N-bis(carboxymethyl)aminomethyl]-4'-(p-nitrobenzyl)-2'-pyridyl}-4-{6"-[N,N-bis(carboxymethyl)aminomethyl]-2"-pyridyl}thiazole (39).

This compound (39) was synthesized using a method analogous to the synthesis described in Example 9. The yield was 100%.

$^1$H NMR (400 MHz DMSO-d$_6$): 3.55 (4H, s); 3.60 (4H, s); 3.99 (2H, s); 4.06 (2H, s); 4.10 (2H, s); 7.52–7.65 (7H, m); 8.09–8.22 (3H, m) UV ($\lambda_{max}$ in water as free ligand): 285, 265 & 245 nm UV ($\lambda_{max}$ in water as europium(III) chelate): 320(sh) & 285 nm Scheme 7. The synthesis of compound 42

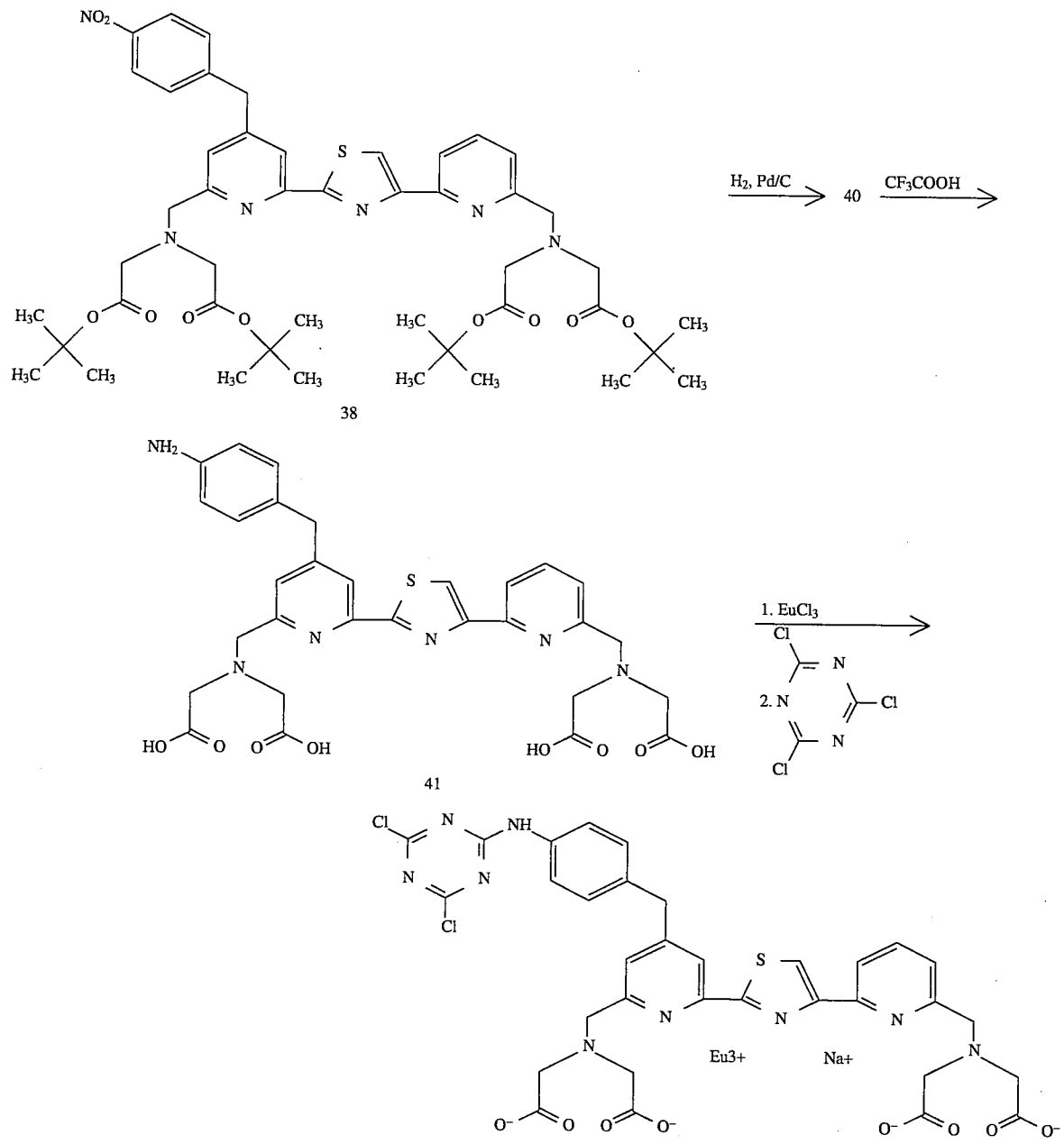

EXAMPLE 40

The synthesis of 2-{4'-(p-aminobenzyl)-6'-[N,N-bis(tert-butoxycarbonylmethyl)aminomethyl]-2'-pyridyl}-4-{6"-[N,N-bis(tert-butoxycarbonylmethyl)aminomethyl]-2"-pyridyl}-thiazole (40).

A mixture of compound 38 (150 mg, 0.17 mmol), 10% palladium on carbon (10 mg) and methanol (30 ml) was stirred for five hours under a hydrogen atmosphere (690 kPa). After filtration and evaporation of the filtrate, the product was purified with flash chromatography (silica, petroleum ether/ethyl acetate, 5/3.). The yield was 40 mg (27%).

$^1$H NMR (60 MHz, CDCl$_3$): 45 (36H, s); 3.51 (8H, s); 3.77 (2H, s); 3.92 (2H, s); 4.06 (2H, s); 6.64–8.03 (9H, m); 8.15 (1H, s)

EXAMPLE 41

The synthesis of 2-{4'-(p-aminobenzyl)-6'-[N,N-bis(carboxymethyl) aminomethyl]-2'-pyridyl}-4-{6"-[N,N-bis(carboxymethyl)aminomethyl]-2"-pyridyl}thiazole (41).

This compound (41) was synthesized using a method analogous to the synthesis described in Example 9. The yield was 100%.

UV ($\lambda_{max}$ in water as free ligand): 315 & 290 nm

UV ($\lambda_{max}$ in water as europium(III) chelate): 325 & 290 nm

EXAMPLE 42

The synthesis of europium(III) chelate of 2-{4'-[p-(4,6-dichlorotriazon-2-ylamino)benzyl)-6'-[N,N-bis(carboxymethyl)aminomethyl]-2'-pyridyl}-4-{6"-[N,N-bis(carboxymethyl)aminomethyl]-2"-pyridyl}thiazole (42).

The compound 41 (25 mg, 40 µmol) was dissolved in water (700 µl) and the pH was adjusted to 6.5 with solid sodium bicarbonate. Europium (III) chloride (22 mg, 60 µmol) in water (200 µl) was added during 15 minutes and the pH was maintained at 5–7. After stirring for 1.5 hours, the pH was raised to 8.5 with 1M sodium hydroxide and the precititate was filtered off. The filtrate was triturated with acetone, the precipitate was filtered and washed with acetone. A mixture of 2,4,6-trichlorotriazine (2 mg, 10 µmol), acetone (100 µl) and water (100 µl) was added to a solution of the europium(III) chelate (8 mg, 10 µl) and 0.1M sodium acetate (150 µl, pH 4.9). After stirring for 15 minutes, the reaction mixture was triturated with acetone. The precipitate was filtered off, washed with acetone and dried in an exsiccator.

UV ($\lambda_{max}$ in water): 331, 287 & 250 nm

Scheme 6.
The synthesis of compounds 49 and 56

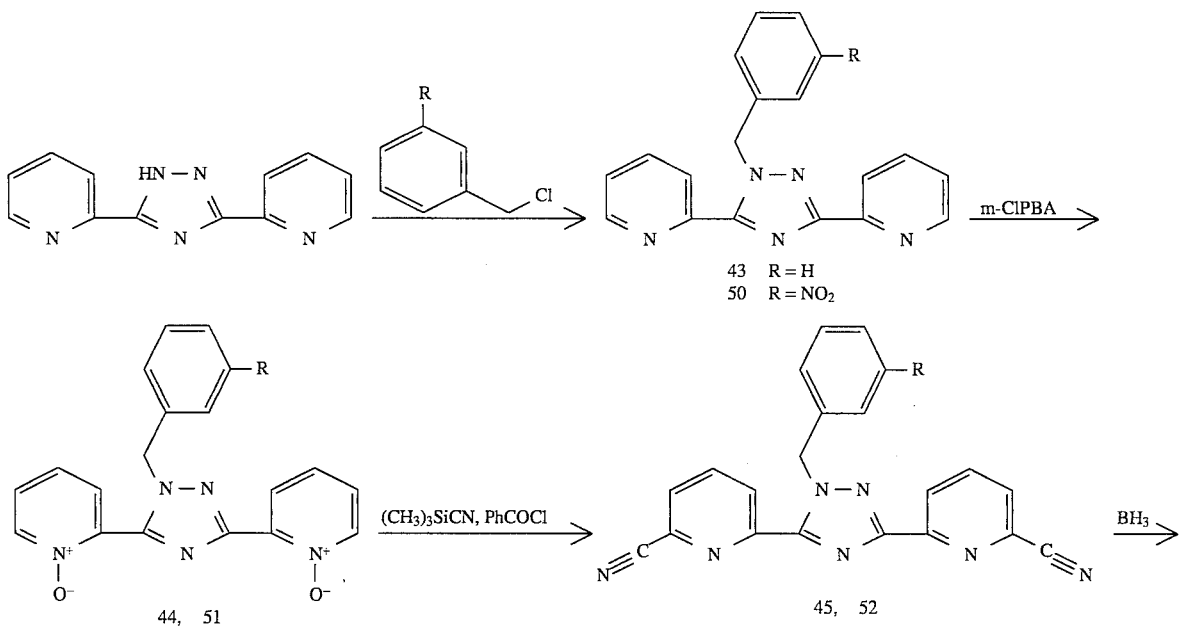

Scheme 6.
The synthesis of compounds 49 and 56

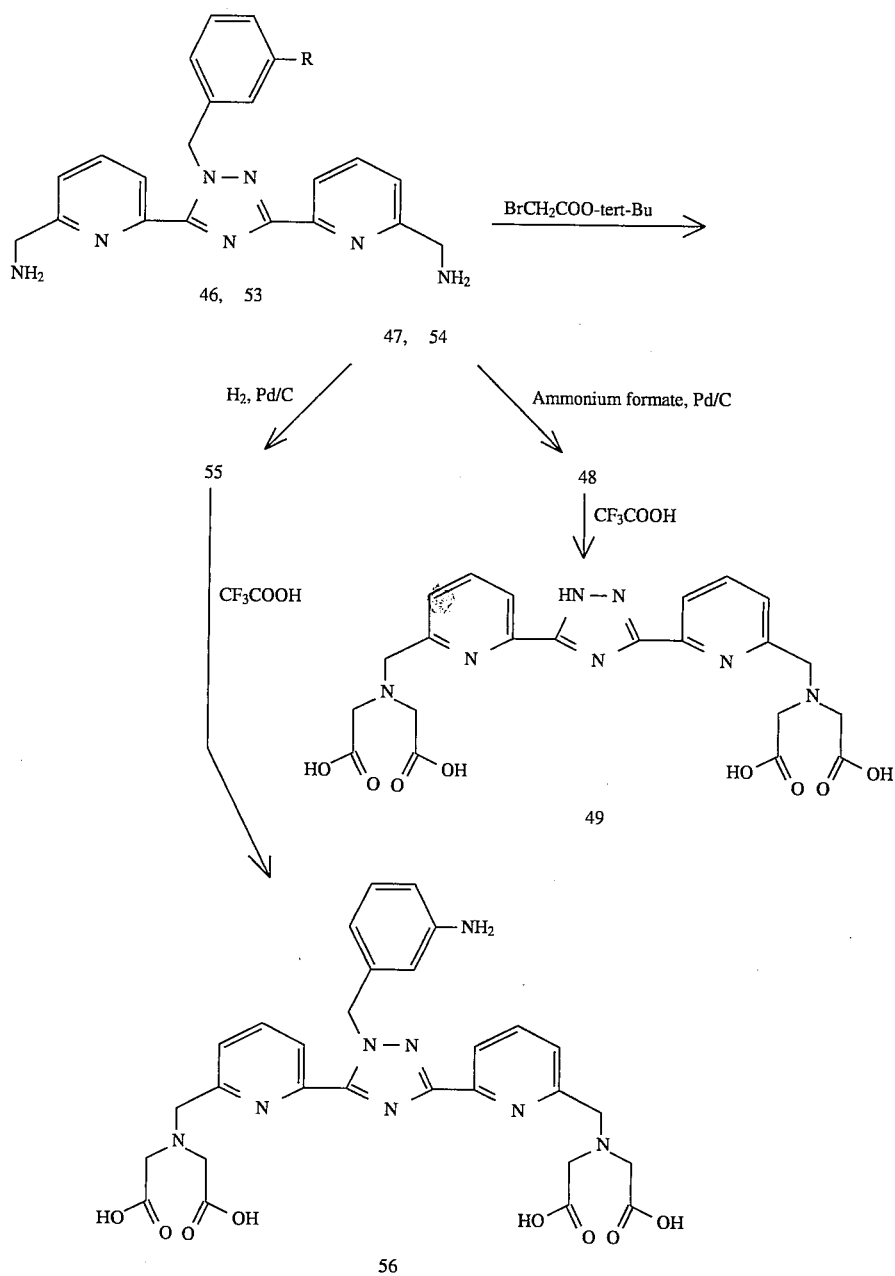

EXAMPLE 43

The synthesis of 1-benzyl-3,5-di(2'-pyridyl)-1,2,4-triazole (43).

A mixture of 3,5-di(2'-pyridyl)-1,2,4-triazole (1.12 g, 5.00 mmol), potassium carbonate (1.38 g, 10.0 mmol), benzylchloride (0.63 g, 5.0 mmol) and acetonitrile (65 ml) was refluxed for 2.5 hours. The reaction mixture was filtered and the filtrate was evaporated to dryness. The product was purified with flash chromatography (silica, 1% methanol in dichloromethane). The yield was 1.05 g (67%).

$^1$H NMR (60 MHz, CDCl$_3$): 6.20 (2H, s); 6.93–7.38 (6H, m); 7.58–7.93 (3H, m); 8.15–8.79 (4H, m)

EXAMPLE 44

The synthesis of 1-benzyl-3,5-di(2'-pyridyl)-1,2,4-triazole N', N'-dioxide (44).

This compound (44) was synthesized using a method analogous to the synthesis described in Example 19. The reaction time was 11 days at room temperature. The product was purified with flash chromatography (silica, 2, 5 and 10% methanol in chloroform). The yield was 62%.

$^1$H NMR (60 MHz, CDCl$_3$): 5.76 (2H, s); 7.14–7.41 (9H, m); 7.97–8.45 (4H, m)

EXAMPLE 45

The synthesis of 1-benzyl-3,5-bis(6'-cyano-2'-pyridyl)-1, 2,4-triazole (45).

This compound (45) was synthesized using a method analogous to the synthesis described in Example 36. The field was 71%.

$^1$H NMR (400 MHz, CDCl$_3$): 6.15 (9H, s); 7.26 (2H, t, J=7 Hz): 7.32 (2H, t, J=7 Hz); 7.42 (2H, d, J=7 Hz); 7.75–7.78 (2H, m); 7.79 (1H, t, J=8 Hz); 8.01 (1H, t, J=8 Hz); 8.47 (1H, dd, J=1 & 8 Hz); 8.64 (1H, dd, J=1 & 8 Hz)

EXAMPLE 46

The synthesis of 3,5-bis(6'-aminomethyl]-2'-pyridyl)-1-benzyl-1,2,4-triazole pentahydrochloride (46).

This compound (46) was synthesized using a method analogous the synthesis described in Example 37. The field was 100%.

$^1$H NMR (400 MHz, CDCl$_3$): 4.26 (2H, s); 4.28 (2H, s); 5.87 (2H, s); 7.03–7.50 (m, 7H); 7.88–8.03 (4H, m)

EXAMPLE 47

The synthesis of 1-benzyl-3,5-bis{6'-bis[N,N-bis(tert-butoxycarbonylmethyl)aminomethyl]-2'-pyridyl}-1,2,4-triazole (47).

This compound (47) was synthesized using a method analogous to the synthesis described in Example 22. The product was purified with flash chromatography (silica, petroleum ether/ethyl acetate, 1/1). The yield was 39%.

$^1$H NMR (60 MHz, CDCl$_3$): 1.45 (36H, s); 3.47 (4H, s); 3.52 (4H, s); 4.08 (2H, s); 4.21 (2H, s); 6.20 (2H, s); 7.13–7.30 (5H, m); 7.54–7.83 (4H, m); 7.95–8.33 (2H, m)

EXAMPLE 48

The synthesis of 3,5-bis{6'-bis[N,N-bis(tert-butoxycarbonylmethyl)aminomethyl]-2'-pyridyl}-1,2,4-triazole (48).

A mixture of compound 47 (0.44 g, 0.53 mmol), 10% palladium on carbon (0.25 g), ammonium formate (about 1.0 g, 15 mmol) and methanol (10 ml) under a nitrogen atmosphere was stirred for several days at room temperature. The reaction mixture was filtered and the filtrate was evaporated to dryness. The residue was dissolved in chloroform (50 ml), washed with water (20 ml) and dried with sodium sulfate. The yield was 0.34 g (87%).

$^1$H NMR (60 MHz, CDCl$_3$): 1.46 (36H, s); 3.35 (4H, s); 3.52 (4H, s) 4.12 (2H, s); 4.17 (2H, s); 7.57–8.25 (6H, m)

EXAMPLE 49

The synthesis of 3,5-bis{6'-bis[N,N-bis(carboxymethyl)aminomethyl]-2'-pyridyl}-1,2,4-triazole (49).

This compound (49) was synthesized using a method analogous to the synthesis described in Example 9. The yield was 100%.

UV ($\lambda_{max}$ in water as free ligand): 284 & 232 nm

UV ($\lambda_{max}$ in water as europium chelate): 288 & 233 nm

EXAMPLE 50

The synthesis of 1-(m-nitrobenzyl)-3,5-di(2'-pyridyl)-1,2,4-triazole (50).

This compound (50) was synthesized using a method analogous to the synthesis described in Example 43. The yield was 78%.

$^1$H NMR (60 MHz, CDCl$_3$): 6.27 (2H, s); 7.20–7.86 (6H, m); 7.91–8.52 (4H, m); 8.62–8.80 (2H, m)

EXAMPLE 51

The synthesis of 1-(m-nitrobenzyl)-3,5-di(2'-pyridyl)-2,4-triazole N', N'-dioxide (51).

This compound (51) was synthesized using a method analogous to the synthesis described in Example 44. The product was purified with flash chromatography (silica, 3,7 and 0% methanol in chloroform). The yield was 51%.

$^1$H NMR (60 MHz, CDCl$_3$): 5.80 (2H, s); 7.05–8.05 (10H, m); 8.32–8.53 (1H, m); 9.29 (1H, m) mol wt (MS): 390 (M$^+$)

EXAMPLE 52

The synthesis of 3,5-bis(6'-cyano-2'-pyridyl)-1-(m-nitrobenzyl)-1,2,4-triazole (52).

This compound (52) was synthesized using a method analogous to the synthesis described in Example 36. The product was purified with flash chromatography (silica, ethyl acetate). The yield was 55%.

$^1$H NMR (60 MHz, CDCl$_3$): 6.24 (2H, s); 7.52–8.24 (8H, m); 8.48 (1H, dd); 8.70 (1H, dd) UV ($\lambda_{max}$ in ethanol): 287 (sh) & 254 nm mol wt (MS): 408 (M$^+$)

EXAMPLE 53

The synthesis of 3,5-bis(6'-aminomethyl-2'-pyridyl)-1-(m-nitrobenzyl)-1,2,4-triazole pentahydrochloride (53).

This compound (53) was synthesized using a method analogous to the synthesis described in Example 37. The yield was 82%.

$^1$H NMR (60 MHz, CDCl$_3$): 4.25 (4H, s); 5.97 (2H, s); 7.20–8.05 (10H, m)

EXAMPLE 54

The synthesis of 3,5-bis{6'-bis[N,N-bis(tert-butoxycarbonylmethyl)aminomethyl]-2'-pyridyl}-1-(m-nitrobenzyl)-1,2,4-triazole (54).

This compound (54) was synthesized using a method analogous to the synthesis described in Example 22. The product was purified with flash chromatography (silica, petroleum ether/ethyl acetate, 1/1). The yield was 42%.

$^1$H NMR (60 MHz, CDCl$_3$): 1.44 (18H, s); 1.45 (18H, s); 3.47 (4H, s); 3.52 (4H, s); 4.10 (2H, s); 4.22 (2H, s); 6.32 (2H, s); 7.30–8.39 (10, m) UV ($\lambda_{max}$ in ethanol): 283 & 237 nm

EXAMPLE 55

The synthesis of 1-(m-aminobenzyl)-3,5-bis{6'-bis[N,N-bis(tert-butoxycarbonylmethyl)aminomethyl]-2'-pyridyl}-1,2,4-triazole (55).

This compound (55) was synthesized using a method analogous to the synthesis described in Example 40. The produce was purified with flash chromatography (silica, 5% methanol in chloroform). The yield was 85%.

$^1$H NMR (60 MHz, CDCl$_3$): 1.45 (36H, s); 3.48 (4H, s); 3.52 (4H, s); 4.10 (2H, s); 4.22 (2H, s); 6.10 (2H, s); 6.41–7.01 (4H, m); 7.70–8.33 (6H, m)

EXAMPLE 56

The synthesis of 1-(m-aminobenzyl)-3,5-bis{6'-bis[N,N-bis(carboxymethyl) aminomethyl]-2'-pyridyl}-1,2,4-triazole (56).

This compound (56) was synthesized using a method analogous to the synthesis described in Example 9. The yield was 100%.

$^1$H NMR (400 MHz, DMSO-$d_6$): 3.54 (4H, s); 3.62 (4H, s); 4.09 (2H, s); 4.14 (2H, s); 6.10 (2H, s); 6.80–6.88 (2H, m); 6.96–7.02 (1H, m); 7.19–7.23 (1H, m); 7.69 (1H, d); 7.73 (1H, d); 7.97 (1H, t); 8.04 (1H, d); 8.05 (1H, d); 8.17 (1H, d)

UV ($\lambda_{max}$ in water as free ligand): 282 & 234 nm

UV ($\lambda_{max}$ in water as europium(III) chelate): 293, 282 & 236 nm

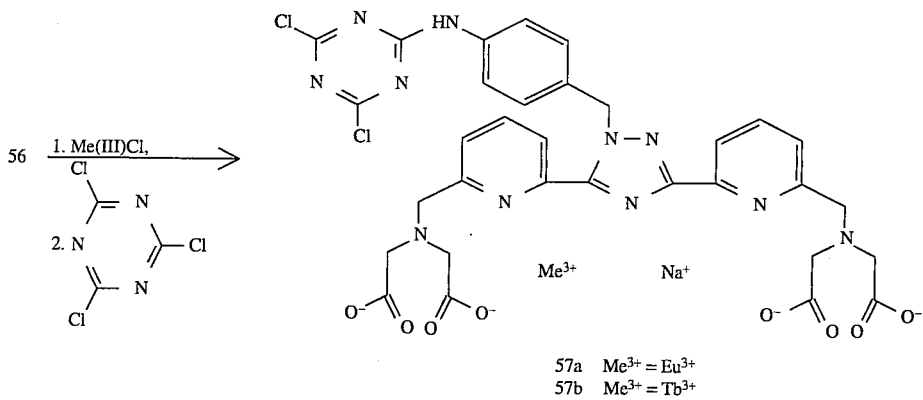

Scheme 9.
The synthesis of compounds 57a and 57b

57a  Me$^{3+}$ = Eu$^{3+}$
57b  Me$^{3+}$ = Tb$^{3+}$

EXAMPLE 57a

The synthesis of europium(III) chelate of 1-[(m-(4,6-dichlorotriazon-2-ylamino)benzyl]-3,5-bis{6'-bis[N,N-bis-(carboxymethyl)aminomethyl]-2'-pyridyl}-1,2,4-triazole (57a).

This compound (57a) was synthesized using a method analogous to the synthesis described in Example 42.

UV ($\lambda_{max}$ in water): 295(sh), 282 & 236 nm.

EXAMPLE 57b

The synthesis of terbium(III) chelate of 1-[m-(4,6-dichlorotriazon-2-ylamino)benzyl]-3,5-bis{6'-bis[N,N-bis(carboxymethyl)aminomethyl]-2'-pyridyl}-1, 2,4-triazole (58).

This compound (57b) was synthesized using a method analogous to the synthesis described in Example 42.

UV ($\lambda_{max}$ in water): 295(sh), 282 & 237 nm.

Scheme 10. The synthesis of compound 68
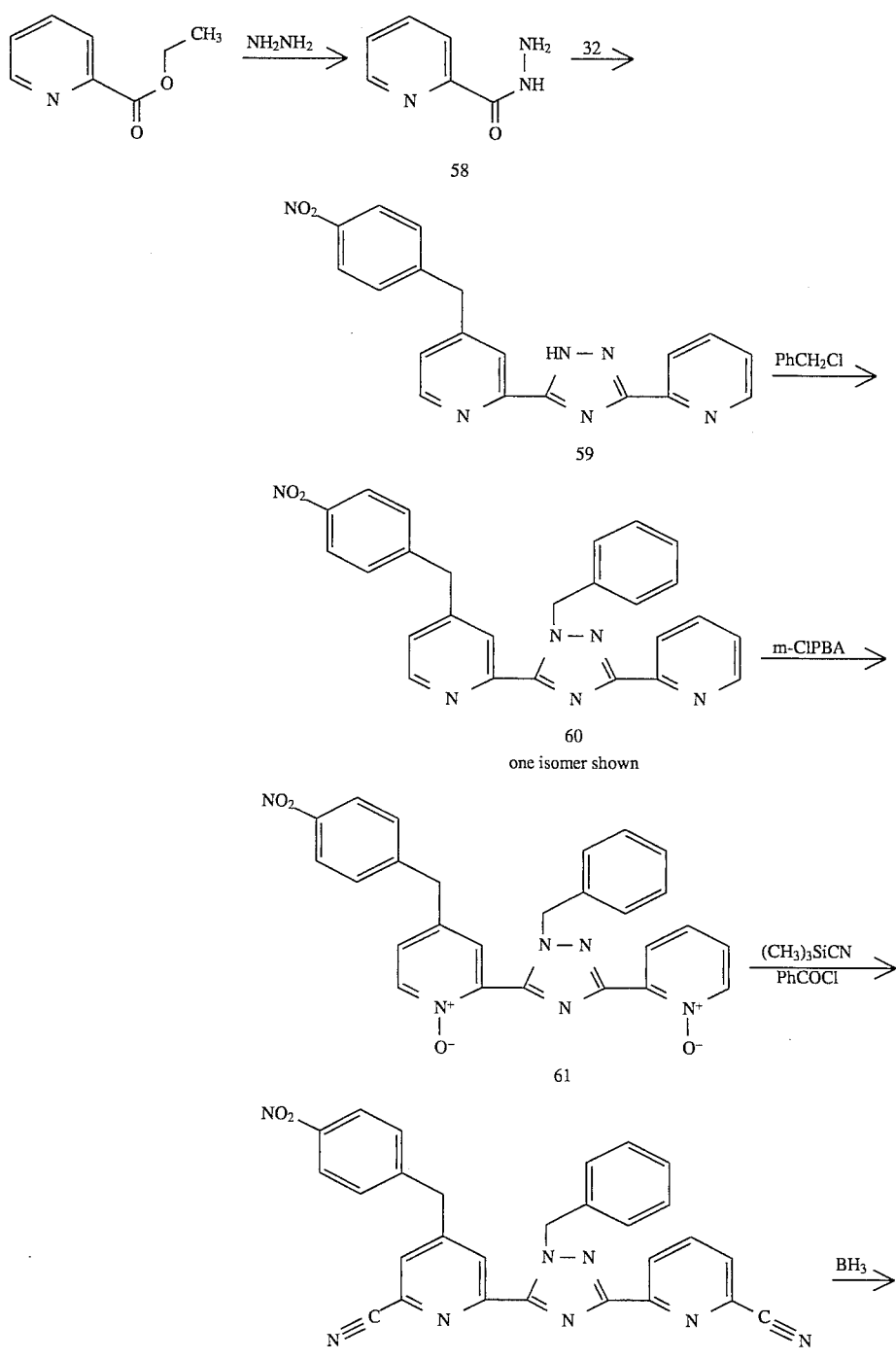

-continued
Scheme 10. The synthesis of compound 68

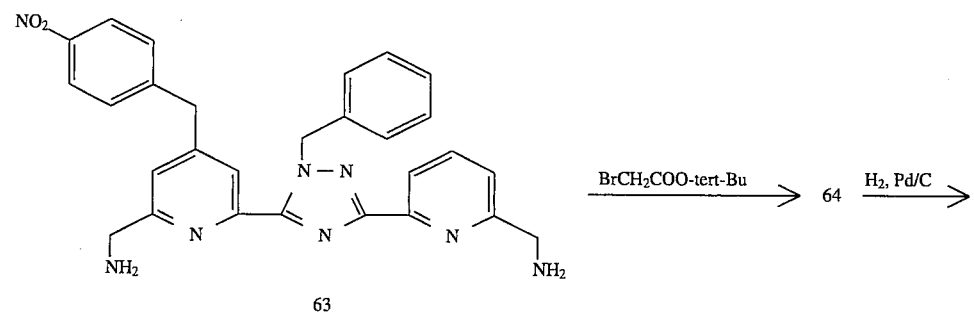

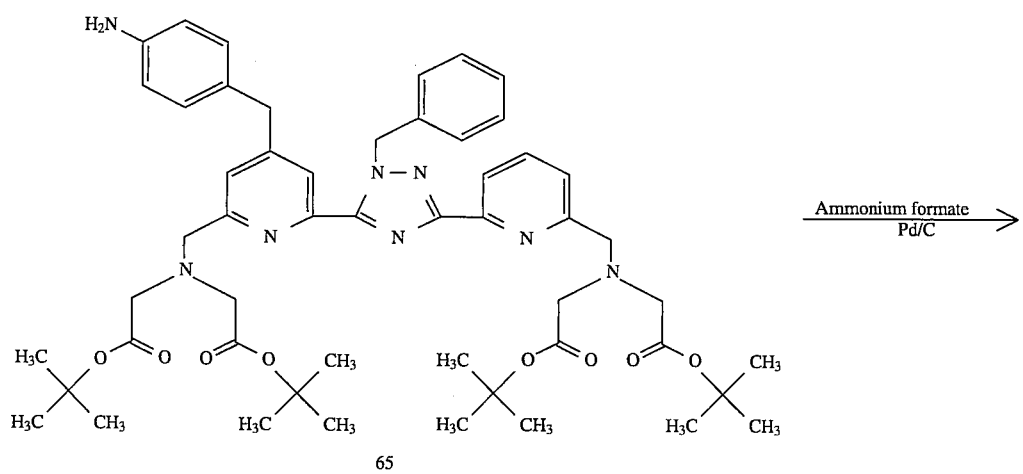

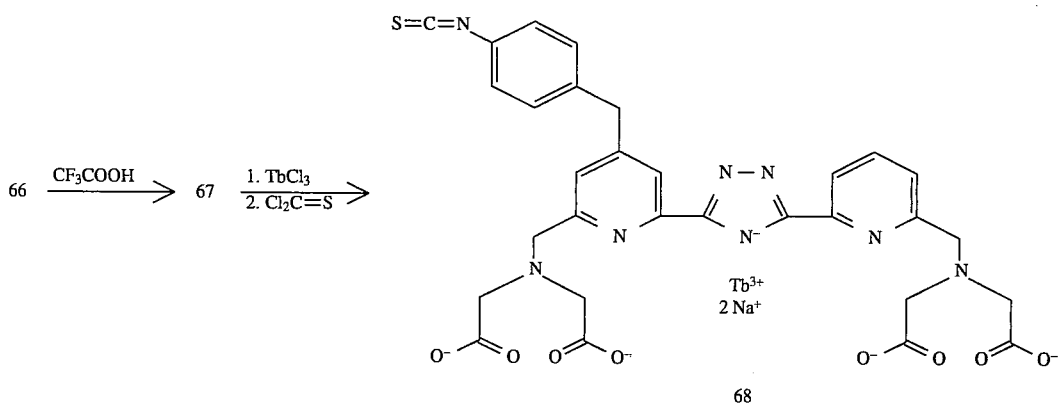

EXAMPLE 58

The synthesis of 2-pyridylhydrazide (58).

Hydrazine hydrate (17.5 ml, 500 mmol) in ethanol (50 ml) was added to a solution of ethyl 2-pyridinecarboxylate (7.53 g, 50.0 mmol) and ethanol (25 ml). After evaporation and coevaporation with toluene, the product was crystallized from toluene. The yield was 6.1 g (86% ).

$^1$H NMR (60 MHz, DMSO-$d_6$): 4.49 (3H, bs); 7.44–7.74 (1H, m); 7.94–8.04 (2H, m); 8.56–8.68 (1H, m)

UV ($\lambda_{max}$ in ethanol): 265 & 216 nm

EXAMPLE 59

The synthesis of 3-[4'-(p-nitrobenzyl)-2'-pyridyl]-5-(2''-pyridyl)-1,2,4-triazole (59).

A mixture of compounds 32 (4.80 g, 20.0 mmol) and 58 (2.74 g, 20.0 mmol) was stirred for 24 hours an 160° C. The reaction mixture was treated several times with hoe toluene and the combined toluene fractions were evaporated to dryness. The residue was dissolved in 10% methanol in chloroform, filtered through a short silica column and the filtrate was evaporated to dryness. The yield was 5.6 g (78%).

$^1$H NMR (400 MHz, CDCl$_3$): 4.17 (2H, s); 7.20 (1H, d, J=4.7 Hz); 7.33–7.39 (1H, m); 7.39 (2H, d, J=8.4 Hz); 7.85–7.90 (1H, m); 8.18 (2H, d, J=8.4 Hz); 8.25 (1H, s); 8.35 (1H, d, J=8.1 Hz); 8.72 (1H, d, J=5.0 Hz); 8.78 (1H, d, J=4.7 Hz) UV ($\lambda_{max}$ in ethanol): 275 nm

EXAMPLE 60

The synthesis of 1 (and 2)-benzyl-3-[4'-(p-nitrobenzyl)-2'-pyridyl]-5-(2''-pyridyl)-1,2,4-triazole (60).

This compound (60) was synthesized using a method analogous to the synthesis described in Example 43. The yield was 76%.

$^1$H NMR (60 MHz, CDCl$_3$): 4.12 (2H, s); 6.19 (2H, s); 6.86–8.73 (16H, m) UV ($\lambda_{max}$ in ethanol): 279 nm

EXAMPLE 61

The synthesis of 1 (and 2)-benzyl-3-[4'-(p-nitrobenzyl)-2'-pyridyl]-5-(2"-pyridyl)-1,2,4-triazole N',N"-dioxide (61).

This compound (61) was synthesized using a method analogous to the synthesis described in Example 44. The product was purified with flash chromatography (silica, 2, 5 and 10% methanol in chloroform). The yield was 50%.

$^1$H NMR (400 MHz, CDCl$_3$, aliphatic area, isomer 1): 3.96 (2H, s); 5.79 (2H, s)

$^1$H NMR (400 MHz, CDCl$_3$, aliphatic area, isomer 2): 4.10 (2H, s); 5.75 (2H, s)

EXAMPLE 62

The synthesis of 1 (and 2)-benzyl-3-[6'-cyano-4'-(p-nitrobenzyl)-2'-pyridyl]-5-(6"-cyano-2"-pyridyl)-1,2,4-triazole (62).

This compound (62) was synthesized using a method analogous to the synthesis described in Example 36. The product was purified with flash chromatography (silica, 5/3, 1/1 and 0/1 petroleum ether/ethyl acetate). The yield was 51%.

$^1$H NMR (400 MHz, CDCl$_3$, isomer 1): 4.24 (2H, s); 6.13 (2H, s); 7.27 (1H, t, J=7 Hz); 7.31 (2H, t, J=7 Hz); 7.39 (2H, d, J=7 Hz); 7.41 (2H, d, J=9 Hz); 7.54 (1H, s); 7.76 (1H, d, J=8 Hz); 8.00 (1H, d, J=8 Hz); 8.24 (2H, d, J=9 Hz); 8.29 (1H, s); 8.60 (1H, d, J=8 Hz)

$^1$H NMR (400 MHz, CDCl$_3$, isomer 2): 4.20 (2H, s); 6.13 (2H, s); 7.26 (1H, t, J=7 Hz); 7.31 (2H, t, J=7 Hz); 7.37 (2H, d, J=9 Hz); 7.40 (2H, d, J=7 Hz); 7.50 (1H, s); 7.77 (1H, d, J=8 Hz); 7.99 (1H, t, J=8 Hz); 8.22 (2H, d, J=9 Hz); 8.45 (1H, d, J=8 Hz); 8.54 (1H, s) UV ($\lambda_{max}$ in ethanol): 263 nm

EXAMPLE 63

The synthesis of 3-[6'-aminomethyl-4'-(p-nitrobenzyl)-2'-pyridyl]-5-(6"-aminomethyl-2"-pyridyl)-1(and 2)-benzyl-1,2,4-triazole pentahydrochloride (63).

This compound (63) was synthesized using a method analogous to the synthesis described in Example 37. The yield was 88%. UV ($\lambda_{max}$ in water): 280 & 235(sh)

EXAMPLE 64

The synthesis of 1 (and 2)-benzyl-3-{6'-[N,N-bis(tert-butoxycarbonylmethyl)aminomethyl]-4'-(p-nitrobenzyl)-2"-pyridyl}-5-{6'-[N,N-bis(tert-butoxycarbonylmethyl)aminomethyl]-2'-pyridyl}-1,2,4-triazole (64).

This compound (64) was synthesized using a method analogous to the synthesis described in Example 22. The product was purified with flash chromatography (silica, petroleum ether/ethyl acetate, 1/1). The yield was 44%.

$^1$H NMR (400 MHz, CDCl$_3$, isomer 1, aliphatic area): 1.45 (36H, s); 3.46 (4H, s); 3.48 (4H, s); 4.06 (2H, s); 4.15 (2H, s); 4.19 (2H, s); 6.19 (2 H, s)

$^1$H NMR (400 MHz, CDCl$_3$, isomer 2, aliphatic area): 1.45 (36H, s); 3.44 (4H, s); 3.51 (4H, s); 4.05 (2H, s); 4.12 (2H, s); 4.20 (2H, s); 6.19 (2H, s) UV ($\lambda_{max}$ in ethanol): 283 & 250 nm

EXAMPLE 65

The synthesis of 1 (and 2)-benzyl-3-{6'-[N,N-bis(tert-butoxycarbonylmethyl)aminomethyl]-4'-(p-aminobenzyl)-2'-pyridyl}-5-{6"-[N,N-bis(tert-butoxycarbonylmethyl)aminomethyl]-2"-pyridyl}-1,2,4-triazole (65).

This compound (65) was synthesized using a method analogous to the synthesis described in Example 40. The product was purified with flash chromatography (silica, 2 and 3% methanol in chloroform). The yield was 36%.

$^1$H NMR (400 MHz, CDCl$_3$, isomer 1): 1.45 (36H, s); 3.46 (4H, s); 3.50 (4H, s); 3.93 (2H, s); 4.05 (2H, s); 4.19 (2H, s); 6.19 (2H, s); 6.62 (2H, d, J=8 Hz); 7.01 (2H, d, J=8 Hz); 7.15–7.35 (5H, m); 7.65 (1H, s); 7.71 (1H, d, J=8 Hz); 7.79 (1H, t, J=8 Hz); 7.91 (1H, s); 8.23 (1H, d, J=8 Hz)

$^1$H NMR (400 MHz, CDCl$_3$, isomer 2): 1.45 (36H, s); 3.45 (4H, s); 3.51 (2H, s); 3.90 (2H, s); 4.03 (2H, s); 4.21 (2H, s); 6.19 (2H, s); 6.61 (2H, d, J=8 Hz); 6.98 (2H, d, J=8 Hz); 7.15–7.35 (5H, m); 7.50 (1H, s); 7.78 (1H, t, J=8 Hz); 7.83 (1H, d, J=8 Hz); 8.07 (1H, d, J=8 Hz); 8.12 (1H, s)

EXAMPLE 66

The synthesis of 3-{6'-[N,N-bis(tert-butoxycarbonylmethyl) aminomethyl]-4'-(p-aminobenzyl)-2'-pyridyl}-5-{6" [N,N-bis(tert-butoxycarbonylmethyl)aminomethyl]-2"-pyridyl}-1,2,4-triazole (66).

This compound (66) was synthesized using a method analogous to the synthesis described in Example 48. The yield was 50%. $^1$H NMR (60 MHz, CDCl$_3$, aliphatic area): 1.45 (36H, s); 3.50 (8H, s); 3.91 (2H, s); 4.09 (2H, s); 4.16 (2H, s)

EXAMPLE 67

The synthesis of 3-{6'-[N,N-bis(carboxymethyl)aminomethyl]-4'-(p-aminobenzyl)-2'-pyridyl}-5-{6"-[N,N-bis(carboxymethyl)aminomethyl]-2"-pyridyl}-1,2,4-triazole (67).

This compound (67) was synthesized using a method analogous to the synthesis described in Example 9. The yield was 100%.

EXAMPLE 68

The synthesis of terbium(III) chelate of 3-{6'-[N,N-bis-(carboxymethyl)aminomethyl]-4'-(p-isothiocyanatobenzyl)-2'-pyridyl}-5-{6"-[N,N-bis(carboxymethyl) aminomethyl]-2"-pyridyl}-1,2,4-triazole (68).

Compound 68 (50 mg, 0.08 mmol) was dissolved in water (1.5 ml) and the pH was adjusted to 6.5 with solid sodium bicarbonate Terbium(III) chloride (35 mg, 0.090 mmol) in water (0.5 ml) was added during 15 minutes and the pH was maintained at 5–7. After stirring for 1.5 hours, the pH was raised to 8.5 with 1M sodium hydroxide and the precipitate was filtered off. The filtrated was triturated with acetone, the precipitate was filtered and washed with acetone. An aqueous solution of the precipitate (2.5 ml) was added during 15 minutes to a mixture of thiophosgene (2.5 ul, 0.32 mmol), sodium bicarbonate (34 mg, 0.40 mmol) and chloroform (2.5 ml). After stirring for one hour, the fractions were separated and the water fraction was washed with chloroform (3×1.0 ml). The aqueous solution was triturated with acetone, the precipitate was filtered and washed with acetone. The yield was 38 ms (55%).

Scheme 11. The synthesis of compound 72

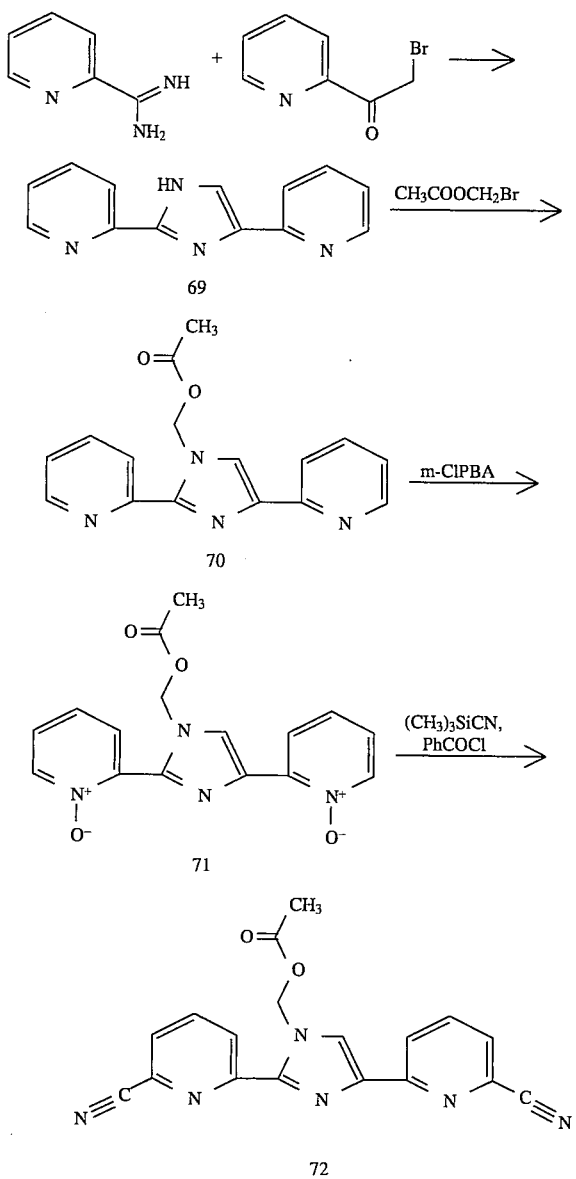

chloroform (50 ml) was refluxed for two hours. The reaction mixture was washed with 5% sodium bicarbonate (20 ml), water (2×20 ml) and dried with sodium sulfate. The product was purified with flash chromatography (silica, ammonia/ 5% methanol in chloroform, first 0/1 then 1/49). The yield was 2.28 g (41%). M.p. 145° C.

$^1$H NMR (400 MHz, CDCl$_3$): 7.15–7.18 (1H, m); 7.27–7.30 (1H, m); 7.72 (2H, t); 7.80 (2H, t); 8.22 (1H, d); 8.58–8.59 (2H, d) UV ($\lambda_{max}$ in ethanol): 307, 260 & 227 nm

EXAMPLE 70

The synthesis of 1-acetoxymethyl-2,4-di(2'-pyridyl)imidazole (70).

A mixture of compound 69 (0.50 g, 2.3 mmol) and potassium carbonate (0.48, 3.4 mmol), bromomethyl acetate (1.03 g, 6.80 mmol) in acetonitrile (20 ml) was refluxed for five hours. After filtration the filtrate was evaporated to dryness. The product was purified with flash chromatography (silica, 2 and 5% methanol in chloroform). The yield was 0.40 g (59%).

$_1$H NMR (400 MHz, CDCl$_3$): 2.07 (3H, s); 6.69 (2H, s); 7.16–7.19 (1H, m); 7.27–7.30 (1H, m); 7.75 (1H, dt, J=1 & 8 Hz); 7.81 (1H, dt, J=1 & 8 Hz); 7.92 (1H, s); 8.07 (1H, d, J=8 Hz); 8.35 (1H, d, J=8 Hz); 8.59–8.61 (2H, m) UV ($\lambda_{max}$ in ethanol): 294, 257 & 223 nm

EXAMPLE 71

The synthesis of 1-acetoxymethyl-2,4-di(2'-pyridyl)imidazole N', N'-dioxide (71).

This compound (71) was synthesized using a method analogous to the synthesis described in Example 44. The product was purified with flash chromatography silica, 2, 5 and 10% methanol in chloroform). The yield was 20%.

$^1$H NMR (400 MHz, CDCl$_3$): 1.98 (3H, s); 6.14 (2H, s); 7.15 (1H, dt); 7.32 (1H, t); 7.40–7.43 (2H, m); 7.72–7.75 (1H, m); 8.31–8.35 (3H, m); 8.92 (1H, s) UV ($\lambda_{max}$ in ethanol): 289(sh), 254 & 220 nm

EXAMPLE 72

The synthesis of 1-acetoxymethyl-2,4-bis(6'-cyano-2'-pyridyl) imidazole (72).

This compound (72) was synthesized using a method analogous to the synthesis described in Example 36. The produce was purified with flash chromatography (silica, petroleum ether/ethyl acetate, 5/3). The yield was 52%. $^1$H NMR (400 MHz, CDCl$_3$): 2.11 (3H, s): 6.61 (2H, s); 7.57 (1H, d, J=8 Hz); 7.71 (1H, d, J=8 Hz); 7.86 (1H, t, J=8 Hz); 7.97 (1H, t, J=8 Hz); 8.04 (1H, s); 8.25 (1H, d, J=8 Hz); 8.57 (1H, d, J=8 Hz) UV ($\lambda_{max}$ in ethanol): 301 & 272 nm

EXAMPLE 69

The synthesis of 2,4-di(2'-pyridyl)imidazole (69).

A mixture of 2-pyridinecarboxamidine hydrochloride (4.85 g, 31.0 mmol), 2-bromoacetylpyridine (5.00 g, 25.0 mmol), N,N-diisopropylethylamine (8.8 ml, 50 mmol) and

Scheme 12 The synthesis of compound 76

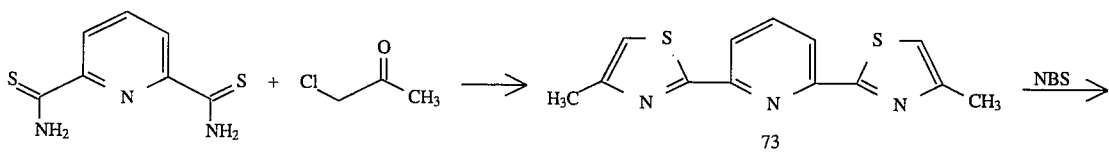

Scheme 12 The synthesis of compound 76

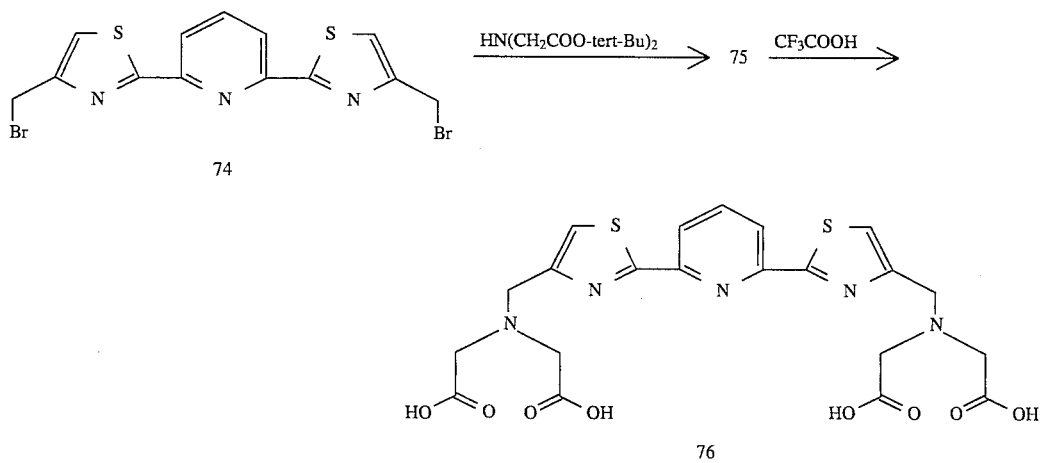

EXAMPLE 73

The synthesis of 2,6-bis(4'-methylthiazol-2'-yl)pyridine (73).

A mixture of 2,6-pyridinedithiodicarboxamide (0.74 g, 3.8 mmol), chloroacetone (0.70 ml, 8.7 mmol) and ethanol (15 ml) was refluxed overnight. Solid material was filtered and washed with ethanol. The suspension of the hydrochloric salt of the product in hot water (50 ml) was alkalized with solid sodium carbonate. The product was filtered and washed with water. The yield was 0.63 g (61%).

$^1$H NMR (400 MHz, CDCl$_3$): 2.54 (6H, s); 7.03 (2H, s); 7.86 (1H, t, J=7.8 Hz); 8.15 (2H, d, J=7.8 Hz) UV ($\lambda_{max}$ in ethanol): 330, 306 & 232 nm

EXAMPLE 74

The synthesis of 2 6-bis(4'-bromomethylthiazol-2'-yl)pyridine (74).

A mixture of compound 73 (0.63 g, 2.3 mmol), N-bromosuccinimide (0.90 g, 5.1 mmol), dibenzoylperoxide (56 mg, 0.2 mmol) and carbon tetrachloride (15 ml) was refluxed overnight.

The reaction mixture was filtered and the filtrate was evaporated Lo dryness. The product was purified with flash chromatography (silica, 2% methanol in chloroform). The yield was 82%.

$^1$H NMR (400 MHz, CDCl$_3$): 4.65 (4H, s); 7.44 (2H, s); 7.93 (1H, t, J=9 Hz); 8.24 (2H, d, J=9 Hz) ($\lambda_{max}$ in ethanol): 328 & 302 nm

EXAMPLE 75

The synthesis of 2,6-bis{4'-[N,N-bis(tert-butoxycarbonylmethyl)aminomethyl]thiazol-2'-yl}pyridine (75).

This compound (75) was synthesized using a method analogous to the synthesis described in Example 8. The product was purified with flash chromatography (silica, petroleum ether/ethyl acetate, first 10/1, then 5/1). The yield was 31%.

$^1$H NMR (400 MHz, CDCl$_3$): 1.48 (36H, s); 3.53 (8H, s); 4.16 (4H, s); 7.42 (2H, s); 7.86 (1H, t, J=8.0 Hz); 8.18 (2H, d, J=8.0 Hz) UV ($\lambda_{max}$ in ethanol): 329 & 299 nm

EXAMPLE 76

The synthesis of 2,6-bis{4'-[N,N-bis(carboxymethyl)aminomethyl]thiazol-2'-yl}pyridine (76).

This compound (76) was synthesized using a method analogous to the synthesis described in Example 9. The yield was 75%.

$^1$H NMR (400 MHz, DMSO-d$_6$): 3.85 (8H, s); 4.33 (4H, s); 7.90 (2H, s) ; 8.18–8.22 (3H, m) UV ($\lambda_{max}$ in water as free ligand): 323 & 287 nm UV ($\lambda_{max}$ in water as europium(III) chelate): 341 & 278 nm

Scheme 13. The synthesis of compound 78

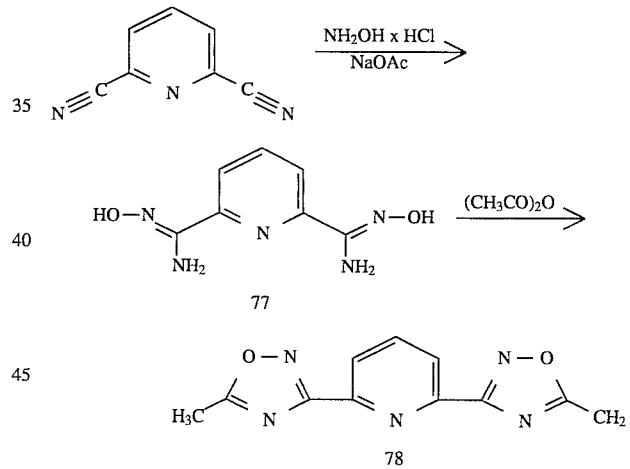

EXAMPLE 77

The synthesis of 2,6-bis(N-hydroxycarboximidamido)pyridine (77).

A mixture of 2,6-dicyanopyridine (8.03 g, 62.2 mmol), hydroxylamine hydrochloride (10.4 g, 150 mmol), sodium acetate (13.8 g, 168 mmol) and water/ethanol (200 ml, 1/5) was refluxed for 45 minutes. After evaporation to dryness the residue was triturated with water, filtered and washed with water. The yield was 11.43 g (94%).

$^1$H NMR (60 MHz, DMSO-d$_6$): 6.26 (4H, bs); 7.70–7.87 (3H, m); 9.83 (2H, s) UV ($\lambda_{max}$ in ethanol): 301 nm

EXAMPLE 78

The synthesis of 2,6-bis(5'-methyl-1',2',4'-oxadiazol-3'-yl)pyridine (78).

A mixture of compound 77 (11.1 g, 57.0 mmol), acetic anhydride (34.9 g, 342 mmol) and toluene (150 ml) was refluxed overnight. After evaporation to half of the original volume, the solid material was filtered and washed with toluene. The yield was 11.6 g (84%).

$^1$H NMR (400 MHz, CDCl$_3$): 2.71 (6H, s); 8.03 (1H, t, J=7.7 Hz); 8.21 (2H, d, J=7.7 Hz) UV ($\lambda_{max}$ in ethanol): 282 & 233 nm Scheme 14. The synthesis of compound 79

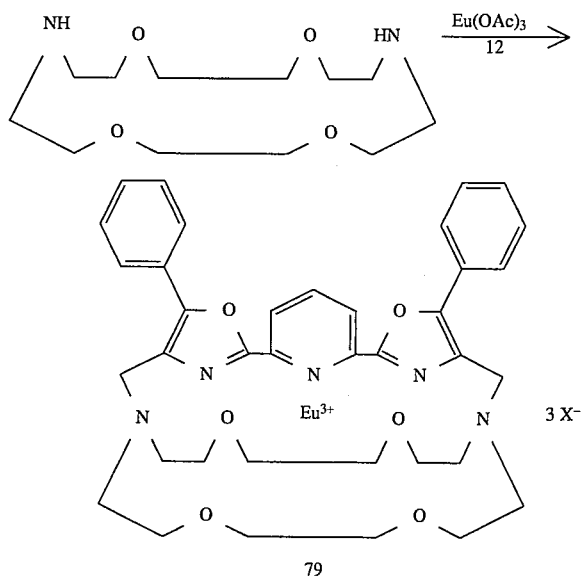

79

EXAMPLE 79

The synthesis of europium(III) cryptate (79).

A mixture of europium(III) acetate (78 mg, 0.24 mmol), trimethyl orthoformate (1.2 ml) and dry acetonitrile (6 ml) was refluxed for two hours. After addition of 1,7,10,16-tetraoxa-4,3-diazacyclooctadecane (62 mg, 0.24 mmol) the reaction mixture was refluxed for 15 minutes. A suspension of compound 12 (130 mg, 0.24 mmol) and dry acetonitrile (4 ml) was added and the reaction mixture was refluxed for 24 hours. The product was filtered and washed with acetonitrile. The yield was 70 mg (37%).

EXAMPLE 80

The synthesis of terbium(III) chelate of 3-{6'-[N,N-bis-(carboxymethyl)aminomethyl]-4'-[p-(4,6-dichlorotriazon-2-ylamino)benzyl ]-2'-pyridyl}-5-{6"-[N,N-bis(carboxymethyl)aminomethyl]-2"-pyridyl}- 1,2,4-triazole (80).

This compound (80) was synthesized from compound 67 using a method analogous to the synthesis described in Example 57b.

EXAMPLE 81

The luminescence properties of europium(III) and terbium(III) chelates of the compound 49.

The relative luminescence yield $\phi_{rel}$ of the europium(III) and terbium(III) chelates of the compound 49 were measured in equimolar 10$^{-5}$M solutions of the compound 49 and the corresponding lanthanide ion. Luminescence measurements were done on a Perkin-Elmer LS-5® spectrofluorometer using the phosphorescence mode which allowed the decay curves of the lanthanide luminescence to be measured. The luminescence yield is reported relative to the luminescence of the uncomplexed lanthanide cation (Ln) using the equation:

$$\phi_{rel} = \frac{I_{che}C_{Ln}k_{Ln}}{I_{Ln}C_{che}k_{che}}$$

where $I_{che}$ and $I_{Ln}$ are the pre-exponential terms of the emission decay curves for the chelated and uncomplexed lanthanide cation, respectively (614 nm for europium and 544 nm for terbium). The excitation wavelength for the uncomplexed europium(III) was 395 nm and for terbium (III) 370 nm $C_{Ln}$ and $C_{che}$ are the concentrations of free and complexed lanthanide cation, respectively, and $k_{Ln}$ and $k_{che}$ the corresponding decay constants. For the europium(III) complex of compound 49 the relative luminescence yield was 1.3×10$^5$ and for the terbium(III) complex it was 5.8× 10$^5$. The excitation wavelength for europium(III) was 280 nm and for terbium(III 310 nm.

EXAMPLE 82

The luminescence properties of europium(III) and terbium(III) chelates of the compound 30.

For the europium(III) complex of compound 30 the relative luminescence yield was 8.9×10$^5$. The excitation wavelength was 336 nm. For terbium(III) the corresponding values were 2.8×10$^3$ and 260 nm.

EXAMPLE 83

The luminescence properties of the europium(III) chelate of the compound 76.

For the europium(III) complex of compound 76 the relative luminescence yield was 5.7×10$^5$. The excitation wavelength was 340 nm.

EXAMPLE 84

The labelling of Rabbit-anti-mouse IgG with compound 68.

IgG fraction of rabbit-anti-mouse-IgG (RAM) (Dako, Denmark) was purified into a labelling buffer consisting of 50 mM carbonate (pH 9.3). RaM fractions (1 mg each) were labelled with chelate 68 using a 100, 300 and 1200 fold molar excess of the chelate in the labelling buffer, incubating at room temperature for 16 hours. Thereafter the IgG-conjugates were purified with a combined column of Trisacryl® GF5 (Reactifs IBF, France) and Sephacryl® S-300 (Pharmacia Biosystems, Sweden), eluting with tris-buffered salt solution (50 mM, pH 7.75). Both the partly aggregated and monomeric IgG fractions were collected and analyzed for protein and terbium(III) concentration. Terbium(III) concentrations were measured with a modified DELFIA® system (Wallace lac, Finland) using 2,4,6-trimethoxyphenyldipicolinic acid as the fluoregenic ligand The incorporation yields varied between 12.2 and

EXAMPLE 85

The relative luminescence of terbium(III)-labelled antibobies.

The relative luminescence of labelled antibodies were measured in different buffers in the pH range between 3.2 and 11.7. The highest luminescences were achieved at neutral pH, at a pH below 5 luminescence decreased rapidly, a pH over 9 the decrease was slow. The luminescence was not quenched by innerfilter effect. The excitation maximum was at 310 nm, producing the typical emission lines at 490 and 544 nm (in addition to minor lines at longer wavelength). The quantum yield compared to the system in Example 83 approached 25% and the decay time was 1.46 ms (in buffer).

EXAMPLE 86

The immunoassay with terbium(III)-labelled antibodies.

The immunoreactivity of the present terbium(III)-labelled antibodies was tested in a model assay system consisting of polystyrene microtitration strips physically coated with monoclonal antibodies (MIgG) using albumin (BSA) coated strips as a control. The strips were incubated in assay buffer (Wallac) containing varying amounts of terbium(III)-labelled RaM. The specific signal ranged from 3000 cps with 1 ng/ml of the terbium(III)-RaM to 1,000,000 cps with 10 μg/ml of terbium(III)-RaM.

Terbium(III)-labelled RaM was also tested in an allergy-specific IgE binding test using a matrix (CAP® matrix, Pharmacia Diagnostics) immobilized with allergenic material. The binding of specific IgE from patient serum was visualized by staining with mouse-anti-human IgE and subsequently with terbium(III)-labelled RaM. The stained matrix was examined with a time-resolved fluorescence microscope and the signal recorded with a CCD camera.

We claim:

1. A luminescent lanthanide chelate consisting of a lanthanide ion and a chelator of the formula

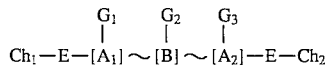

characterized in that a) ~ represents a covalent bond between two carbon atoms;

b) — represents a covalent bond;

c) E represents methylene ($CH_2$) or carbonyl (C=O);

d) $A_1$ is the same as $A_2$, and one or two of $[A_1]$, $[B]$ and $[A_2]$ is/are bivalent heterocyclic unsaturated five-membered rings selected from the group consisting of

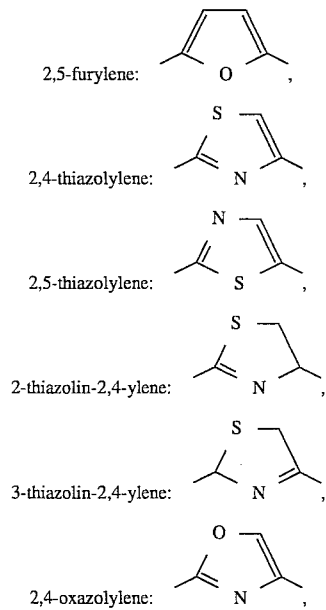

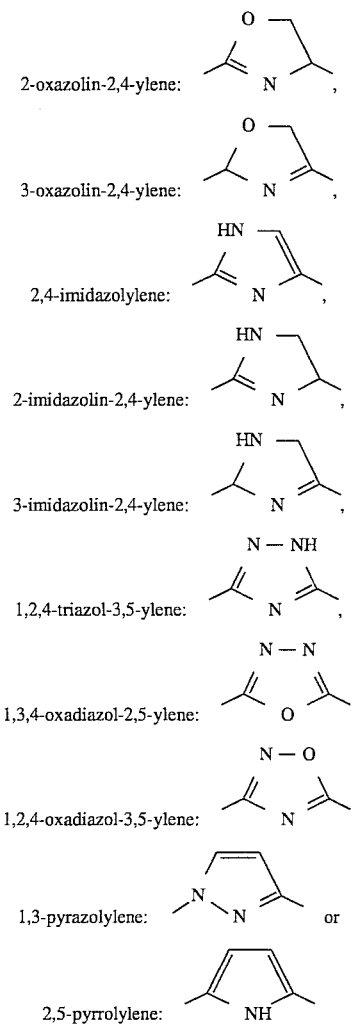

and corresponding rings in which one hydrogen is replaced with the appropriate group $G_1$, $G_2$ or $G_3$, which may be the same or different, the remaining group(s) $[A_1]$, $[B]$ and or $[A_2]$ is/are 2,6-pyridylene or a 2,6-pyridylene ring in which one hydrogen is replaced with the appropriate group $G_1$, $G_2$ or $G_3$ which may be the same or different, one heteroatom in each ring $[A_1]$, $[B]$ and $[A_2]$ coordinates to the same lanthanide ion so that two five-membered rings are formed in which one member of each five-membered ring is the lanthanide ion and two members of each five-membered ring are coordinating heteroatoms of different rings $[A_1]$ and $[B]$ or $[B]$ and $[A_2]$, and e) $Ch_1$ and $Ch_2$ represent identical or different chelating groups, each of which comprises at least two heteroatoms that are coordinated to the lanthanide ion and are selected from the group consisting of oxygen and nitrogen, and at least one of the said coordinating heteroatoms in each of $Ch_1$ and $Ch_2$ forms a five- or six-membered ring together with the lanthanide ion and a coordinating heteroatom of one of $[A_1]$ or $[A_2]$, the distance between each pair of heteroatoms in $Ch_1$ and $Ch_2$ participating in the chelation and forming the same five- or six-membered ring being two or three atoms, respectively, f) $G_1$, $G_2$ and $G_3$, respectively, are selected from the group consisting of hydroxy, nitro, amino, lower alkyl substituted amino, lower aryl substituted amino, lower acyl substituted amino, $C_{1-12}$ alkyl, aryl, alkylaryl, arylalkyl, arylethynyl, alkoxy and aryloxy groups, with the proviso that aryls are selected from the group consisting of phenyl, naphthyl and pyridyl, and an arylalkylene group wherein the alkylene contains from 1 to 8 carbon atoms and from 0 to 4 other atoms selected from the group consisting of oxygen, sulphur, nitrogen and phosphorus, and wherein aryl is selected from the group consisting of phenyl, naphthyl and pyridyl wherein each of said groups $G_1$, $G_2$ and $G_3$ is optionally substituted with a group selected from the group consisting of isothiocyanato, isocyanato, diazonium, bromoacetamido, iodoacetamido, pyridyl-2-dithio, 4-chloro-6-ethoxy-triazon-2-ylamino, 4,6-dichlorotriazon-2-ylamino, amino, aminooxy, carboxyl, hydroxy, aldehyde and mercapto "N-hydroxysuccinimido, 4-nitrophenyl and 2,4-dinitrophenyl ester".

2. The chelate of claim 1, characterized in that [B] is 2,6-pyridylene or the corresponding group in which one hydrogen is replaced with $G_2$.

3. The chelate of claim 1, characterized in that $[A_1]$ and $[A_2]$ are 2,6-pyridylene or the corresponding group in which one hydrogen is replaced with $G_1$ and $G_3$, respectively.

4. The chelate of any of claims 1–3 characterized in that the lanthanide ion is selected from $Eu^{3+}$, $Tb^{3+}$, $Sm^{3+}$ and $Dy^{3+}$.

5. The chelate of claim 1, characterized in that the chelating heteroatoms of $Ch_1$ and $Ch_2$ are selected from primary, secondary or tertiary amino nitrogens and negatively charged oxygens.

6. The chelate of claim 1 characterized in that $Ch_1$ and $Ch_2$ are each independently selected from the group consisting of $N(CH_2COO^-)_2$, $N(CH_2CH_3COO^-)_2$, $N(CH_2PO_3^{2-})_2$ and a 2,6-dicarboxypiperidin-1-yl.

7. The chelate of claim 1 characterized in that $Ch_1$ and $Ch_2$ together form one or two bridges consisting of saturated carbon, ether oxygen and nitrogen atoms, said bridges covalently connecting $[A_1]$ and $[A_2]$ and said nitrogen being selected from secondary or tertiary amino nitrogens.

8. The chelate of claim 1, wherein $Ch_1$ and $Ch_2$ are bonded to one another.

* * * * *